(12) United States Patent
Kraus et al.

(10) Patent No.: US 7,335,816 B2
(45) Date of Patent: Feb. 26, 2008

(54) GLYPHOSATE TOLERANT SUGAR BEET

(75) Inventors: Josef Kraus, Einbeck (DE); Elke Sauerbrey, Einbeck (DE); Reinhard Nehls, Einbeck (DE); Andreas Loock, Einbeck (DE); Rudolf Jansen, Einbeck (DE)

(73) Assignee: KWS SAAT AG, Einbeck (DE)

( * ) Notice: Subject to any disclaimer, the term of this patent is extended or adjusted under 35 U.S.C. 154(b) by 6 days.

(21) Appl. No.: 10/376,763

(22) Filed: Feb. 28, 2003

(65) Prior Publication Data
US 2004/0172669 A1 Sep. 2, 2004

(51) Int. Cl.
*A01H 5/00* (2006.01)
*A01H 5/10* (2006.01)
*C12N 15/82* (2006.01)

(52) U.S. Cl. .................. 800/300; 435/419; 800/298
(58) Field of Classification Search ................ 800/300, 800/267, 298
See application file for complete search history.

(56) References Cited

U.S. PATENT DOCUMENTS 6,204,436 B1 * 3/2001 Mannerloef et al. ........ 800/300

OTHER PUBLICATIONS

Vergunst et al 1999, Critical Reviews in Plant Sciences 18(1): 1-31.*
Biotechnology Consultation Note to the File BNF No. 000090, CFSAN/Office of Food Additive Safety, Aug. 7, 2004, U.S. Food and Drug Administration.*

* cited by examiner

*Primary Examiner*—David H Kruse
(74) *Attorney, Agent, or Firm*—Akerman Senterfitt

(57) ABSTRACT

The invention relates to glyphosate tolerant sugar beet plants, plant material and seeds. It is the object of the invention to provide a transgenic sugar beet plant event that shows a high level of tolerance against glyphosate, but is not impaired in other important agronomic properties such as growth, yield, quality, pathogen resistance etc.

35 Claims, 16 Drawing Sheets

```
GAAATAAAGA TTTCCGAATT AGAATAATTT GTTTATTGCT TTCGCCTATA AATACGACGG    140
GAAATAAAGA TTTCCGAATT AGAATAATTT GTTTATTGCT TTCGCCTATA AATACGACGG   2520

ATCGTAATTT GTCGTTTTAT CAAAATGTAC TTTCATTTTA TAATAACGCT GCGGACATCT    200
ATCGTAATTT GTCGTTTTAT CAAAATGTAC TTTCATTTTA TAATAACGCT GCGGACATCT   2580

ACATTTTTGA ATTGAAAAAA AATTGGTAAT TACTCTTTCT TTTTCTCCAT ATTGACCATC    260
ACATTTTTGA ATTGAAAAAA AATTGGTAAT TACTCTTTCT TTTTCTCCAT ATTGACCATC   2640

ATACTCATTG CTGATCCATG TAGATTTCCC GGACATGAAG CCATTTACAA TTGAATATAT    320
ATACTCATTG CTGATCCATG TAGATTTCCC GGACATGAAG CCATTTACAA TTGAATATAT   2700

CCTAAGTAAA ACCTCATAGG TTTTACGTAT TTCATTTAGG GACTAAAATG GTTTAGGATA    380
           GCCG CTGCCGCTTT GCACCCGGTG GAGCTTGCAT GTTGGTTTCT ACGCAGAACT   2760
```

LB-site genomic DNA

Fig. 11

SEQUENCE LISTING

<160> NUMBER OF SEQ ID NOS: 17

<210> SEQ ID NO 1
<211> LENGTH: 30
<212> TYPE: DNA
<213> ORGANISM: Artificial Sequence
<220> FEATURE:
<221> NAME/KEY: misc_feature
<223> OTHER INFORMATION: Primer

<400> SEQUENCE: 1 ttaattttg caggcgatgg tggctgttat                                      30

<210> SEQ ID NO 2
<211> LENGTH: 30
<212> TYPE: DNA
<213> ORGANISM: Artificial Sequence
<220> FEATURE:
<221> NAME/KEY: misc_feature
<223> OTHER INFORMATION: Primer

<400> SEQUENCE: 2
catacgcatt agtgagtggg ctgtcaggac                                     30

<210> SEQ ID NO 3
<211> LENGTH: 20
<212> TYPE: DNA
<213> ORGANISM: Artificial Sequence
<220> FEATURE:
<221> NAME/KEY: misc_feature
<223> OTHER INFORMATION: Primer

<400> SEQUENCE: 3
atgttatctt taccacagtt                                                20

<210> SEQ ID NO 4
<211> LENGTH: 24
<212> TYPE: DNA
<213> ORGANISM: Artificial Sequence
<220> FEATURE:
<221> NAME/KEY: misc_feature
<223> OTHER INFORMATION: Primer

<400> SEQUENCE: 4
gtccctaaat gaaatacgta aaac                                           24

<210> SEQ ID NO 5
<211> LENGTH: 3778
<212> TYPE: DNA
<213> ORGANISM: Artificial Sequence
<220> FEATURE:
<221> NAME/KEY: misc_feature
<223> OTHER INFORMATION: Inserted DNA with 3' and 5' flanking sequences

<400> SEQUENCE: 5
ctcgagcggc cgccagtgtg atggatatct gcagaattcg cccttatgtt atctttacca      60
cagtttgttg ctctgacaca accggtaaat gcattggcct ttgttttga tggcatcaac      120 tttggagcat ctgattttgc atattcagcc ttttccatgg taattctttt acaagaattt     180
tcattctttc ttaagtataa acacttagct tgggacaaac ttctgatcct atttcttaat     240
ttttgcaggt gatggtggct gttatgagca tttttgtgttt gatgtttctt tcttctcatt   300
acggttttat tgggatctgg gtggctctaa ctatttacat gagcctccgc gcgtttgctg    360

```
aaggcgggaa acgacaatct gatccccatc aagcttgagc tcaggattta gcagcattcc   420
agattgggtt caatcaacaa ggtacgagcc atatcacttt attcaaattg gtatcgccaa   480
aaccaagaag gaactcccat cctcaaaggt ttgtaaggaa gaattctcag tccaaagcct   540
caacaaggtc agggtacaga gtctccaaac cattagccaa aagctacagg agatcaatga   600
agaatcttca atcaaagtaa actactgttc cagcacatgc atcatggtca gtaagtttca   660
gaaaaagaca tccaccgaag acttaaagtt agtgggcatc tttgaaagta atcttgtcaa   720
catcgagcag ctggcttgtg gggaccagac aaaaaaggaa tggtgcagaa ttgttaggcg   780
cacctaccaa aagcatcttt gcctttattg caaagataaa gcagattcct ctagtacaag   840
tggggaacaa aataacgtgg aaaagagctg tcctgacagc ccactcacta atgcgtatga   900
cgaacgcagt gacgaccaca aaagaattcc ctctatataa gaaggcattc attcccacttt   960 gaaggatcat cagatactca accaatcctt ctagaagatc taagcttatc gataagcttg  1020
atgtaattgg aggaagatca aaattttcaa tccccattct tcgattgctt caattgaagt  1080
ttctccgatg gcgcaagtta gcagaatctg caatggtgtg cagaacccat ctcttatctc  1140
caatctctcg aaatccagtc aacgcaaatc tcccttatcg gtttctctga agacgcagca  1200
gcatccacga gcttatccga tttcgtcgtc gtggggattg aagaagagtg ggatgacgtt  1260
aattggctct gagcttcgtc ctcttaaggt catgtcttct gtttccacgg cgtgcatgct  1320
tcacggtgca agcagccgtc cagcaactgc tcgtaagtcc tctggtcttt ctggaaccgt  1380
ccgtattcca ggtgacaagt ctatctccca caggtcctcc atgtttggag gtctcgctag  1440
cggtgaaacc cgtatcaccg gtcttttgga aggtgaagat gttatcaaca ctggtaaggc  1500
tatgcaagct atgggtgcca gaatccgtaa ggaaggtgat acttggatca ttgatggtgt  1560
tggtaacggt ggactccttg ctcctgaggc tcctctcgat ttcggtaacg ctgcaactgg  1620
ttgccgtttg actatgggtc ttgttggtgt ttacgatttc gatagcactt tcattggtga  1680
cgcttctctc actaagcgtc caatgggtcg tgtgttgaac ccacttcgcg aaatgggtgt  1740
gcaggtgaag tctgaagacg gtgatcgtct tccagttacc ttgcgtggac caaagactcc  1800
aacgccaatc acctacaggg tacctatggc ttccgctcaa gtgaagtccg ctgttctgct  1860
tgctggtctc aacaccccag gtatcaccac tgttatcgag ccaatcatga ctcgtgacca  1920
cactgaaaag atgcttcaag gttttggtgc taaccttacc gttgagactg atgctgacgg  1980
tgtgcgtacc atccgtcttg aaggtcgtgg taagctcacc ggtcaagtga ttgatgttcc  2040
aggtgatcca tcctctactg cttttcccatt ggttgctgcc ttgcttgttc caggttccga  2100
cgtcaccatc cttaacgttt tgatgaaccc aacccgtact ggtctcatct tgactctgca  2160
ggaaatgggt gccgacatcg aagtgatcaa cccacgtctt gctggtggag aagacgtggc  2220
tgacttgcgt gttcgttctt ctactttgaa gggtgttact gttccagaag accgtgctcc  2280
ttctatgatc gacgagtatc caattctcgc tgttgcagct gcattcgctg aaggtgctac  2340
cgttatgaac ggtttggaag aactccgtgt taaggaaagc gaccgtcttt ctgctgtcgc  2400
aaacggtctc aagctcaacg gtgttgattg cgatgaaggt gagacttctc tcgtcgtgcg  2460
tggtcgtcct gacggtaagg gtcttcggtaa cgcttctgga gcagctgtcg ctacccacct  2520
cgatcaccgt atcgctatga gcttcctcgt tatgggtctc gtttctgaaa accctgttac  2580
tgttgatgat gctactatga tcgctactag cttcccagag ttcatggatt tgatggctgg  2640
tcttggagct aagatcgaac tctccgacac taaggctgct tgatgagctc aagaattcga  2700
gctcggtacc ggatcctcta gctagagctt tcgttcgtat catcggtttc gacaacgttc  2760
```

-continued

| | |
|---|---|
| gtcaagttca atgcatcagt ttcattgcgc acacaccaga atcctactga gtttgagtat | 2820 |
| tatggcattg ggaaaactgt ttttcttgta ccatttgttg tgcttgtaat ttactgtgtt | 2880 |
| ttttattcgg ttttcgctat cgaactgtga aatggaaatg gatggagaag agttaatgaa | 2940 |
| tgatatggtc cttttgttca ttctcaaatt aatattattt gttttttctc ttatttgttg | 3000 |
| tgtgttgaat ttgaaattat aagagatatg caaacatttt gttttgagta aaaatgtgtc | 3060 |
| aaatcgtggc ctctaatgac cgaagttaat atgaggagta aaacacttgt agttgtacca | 3120 |
| ttatgcttat tcactaggca acaaatatat tttcagacct agaaaagctg caaatgttac | 3180 |
| tgaatacaag tatgtcctct tgtgttttag acatttatga actttccttt atgtaatttt | 3240 |
| ccagaatcct tgtcagattc taatcattgc tttataatta tagttatact catggatttg | 3300 |
| tagttgagta tgaaaatatt ttttaatgca ttttatgact tgccaattga ttgacaacat | 3360 |
| gcatcaatcg acctgcagcc actcgaagcg gccgccactc gagtggtggc cgcatcgatc | 3420 |
| gtgaagtttc tcatctaagc ccccatttgg acgtgaatgt agacacgtcg aaataaagat | 3480 |
| ttccgaatta gaataatttg tttattgctt tcgcctataa atacgacgga tcgtaatttg | 3540 |
| tcgtttatc aaaatgtact ttcattttat aataacgctg cggacatcta cattttgaa | 3600 |
| ttgaaaaaaa ttggtaatta ctctttcttt ttctccatat tgaccatcat actcattgct | 3660 |
| gatccatgta gatttcccgg acatgaagcc atttacaatt gaatatatcc taagtaaaac | 3720 |
| ctcataggtt ttacgtattt catttaggga caagggcgaa ttccagcaca ctggcggc | 3778 |

<210> SEQ ID NO 6
<211> LENGTH: 3706
<212> TYPE: DNA
<213> ORGANISM: Artificial Sequence
<220> FEATURE:
<221> NAME/KEY: misc_feature
<223> OTHER INFORMATION: PCR product

<400> SEQUENCE: 6

| | |
|---|---|
| atgttatctt taccacagtt tgttgctctg acacaaccgg taaatgcatt ggcctttgtt | 60 |
| tttgatggca tcaactttgg agcatctgat tttgcatatt cagccttttc catggtaatt | 120 |
| cttttacaag aattttcatt cttttcttaag tataaacact tagctgggga caaacttctg | 180 |
| atcctatttc ttaattttttg caggtgatgg tggctgttat gagcattttg tgtttgatgt | 240 |
| ttctttcttc tcattacggt tttattggga tctgggtggc tctaactatt tacatgagcc | 300 |
| tccgcgcgtt tgctgaaggc gggaaacgac aatctgatcc ccatcaagct tgagctcagg | 360 |
| atttagcagc attccagatt gggttcaatc aacaaggtac gagccatatc actttattca | 420 |
| aattggtatc gccaaaacca agaaggaact cccatcctca aaggtttgta aggaagaatt | 480 |
| ctcagtccaa agcctcaaca aggtcagggt acagagtctc caaaccatta gccaaaagct | 540 |
| acaggagatc aatgaagaat cttcaatcaa gtaaactac tgttccagca catgcatcat | 600 |
| ggtcagtaag tttcagaaaa agacatccac cgaagactta agttagtgg gcatctttga | 660 |
| aagtaatctt gtcaacatcg agcagctggc ttgtggggac cagacaaaaa aggaatggtg | 720 |
| cagaattgtt aggcgcacct accaaaagca tctttgcctt tattgcaaag ataaagcaga | 780 |
| ttcctctagt acaagtgggg aacaaaataa cgtggaaaag agctgtcctg acagcccact | 840 |
| cactaatgcg tatgacgaac gcagtgacga ccacaaaaga attccctcta taagaagg | 900 |
| cattcattcc catttgaagg atcatcagat actcaaccaa tccttctaga agatctaagc | 960 |
| ttatcgataa gcttgatgta attggaggaa gatcaaaatt ttcaatcccc attcttcgat | 1020 |

-continued

```
tgcttcaatt gaagtttctc cgatggcgca agttagcaga atctgcaatg gtgtgcagaa    1080
cccatctctt atctccaatc tctcgaaatc cagtcaacgc aaatctccct tatcggtttc    1140
tctgaagacg cagcagcatc cacgagctta tccgatttcg tcgtcgtggg gattgaagaa    1200
gagtgggatg acgttaattg gctctgagct tcgtcctctt aaggtcatgt cttctgtttc    1260
cacggcgtgc atgcttcacg gtgcaagcag ccgtccagca actgctcgta agtcctctgg    1320
tctttctgga accgtccgta ttccaggtga caagtctatc tcccacaggt ccttcatgtt    1380
tggaggtctc gctagcggtg aaacccgtat caccggtctt ttggaaggtg aagatgttat    1440
caacactggt aaggctatgc aagctatggg tgccagaatc cgtaaggaag gtgatacttg    1500
gatcattgat ggtgttggta acggtggact ccttgctcct gaggctcctc tcgatttcgg    1560
taacgctgca actggttgcc gtttgactat gggtcttgtt ggtgtttacg atttcgatag    1620
cactttcatt ggtgacgctt ctctcactaa gcgtccaatg ggtcgtgtgt tgaacccact    1680
tcgcgaaatg ggtgtgcagg tgaagtctga agacggtgat cgtcttccag ttaccttgcg    1740
tggaccaaag actccaacgc caatcaccta cagggtacct atggcttccg ctcaagtgaa    1800
gtccgctgtt ctgcttgctg gtctcaacac cccaggtatc accactgtta tcgagccaat    1860
catgactcgt gaccacactg aaaagatgct tcaaggtttt ggtgctaacc ttaccgttga    1920
gactgatgct gacggtgtgc gtaccatccg tcttgaaggt cgtggtaagc tcaccggtca    1980
agtgattgat gttccaggtg atccatcctc tactgctttc ccattggttg ctgccttgct    2040
tgttccaggt tccgacgtca ccatccttaa cgttttgatg aacccaaccc gtactggtct    2100
catcttgact ctgcaggaaa tgggtgccga catcgaagtg atcaacccac gtcttgctgg    2160
tggagaagac gtggctgact gcgtgttcg ttcttctact ttgaagggtg ttactgttcc    2220
agaagaccgt gctccttcta tgatcgacga gtatccaatt ctcgctgttg cagctgcatt    2280
cgctgaaggt gctaccgtta tgaacggttt ggaagaactc cgtgttaagg aaagcgaccg    2340
tctttctgct gtcgcaaacg gtctcaagct caacggtgtt gattgcgatg aaggtgagac    2400
ttctctcgtc gtgcgtggtc gtcctgacgg taagggtctc ggtaacgctt ctggagcagc    2460
tgtcgctacc cacctcgatc accgtatcgc tatgagcttc ctcgttatgg gtctcgtttc    2520
tgaaaaccct gttactgttg atgatgctac tatgatcgct actagcttcc cagagttcat    2580
ggatttgatg gctggtcttg gagctaagat cgaactctcc gacactaagg ctgcttgatg    2640
agctcaagaa ttcgagctcg gtaccggatc ctctagctag agctttcgtt cgtatcatcg    2700
gtttcgacaa cgttcgtcaa gttcaatgca tcagtttcat tgcgcacaca ccagaatcct    2760
actgagtttg agtattatgg cattgggaaa actgttttc ttgtaccatt tgttgtgctt    2820
gtaatttact gtgtttttta ttcggttttc gctatcgaac tgtgaaatgg aaatggatgg    2880
agaagagtta atgaatgata tggtccttt gttcattctc aaattaatat tatttgtttt    2940
ttctcttatt tgttgtgtgt tgaatttgaa attataagag atatgcaaac attttgtttt    3000
gagtaaaaat gtgtcaaatc gtggcctcta atgaccgaag ttaatatgag gagtaaaaca    3060
cttgtagttg taccattatg cttattcact aggcaacaaa tatattttca gacctagaaa    3120
agctgcaaat gttactgaat acaagtatgt cctcttgtgt tttagacatt tatgaacttt    3180
cctttatgta attttccaga atccttgtca gattctaatc attgctttat aattatagtt    3240
atactcatgg atttgtagtt gagtatgaaa atatttttta atgcatttta tgacttgcca    3300
attgattgac aacatgcatc aatcgacctg cagccactcg aagcggccgc cactcgagtg    3360
```

```
gtggccgcat cgatcgtgaa gtttctcatc taagccccca tttggacgtg aatgtagaca    3420
cgtcgaaata aagatttccg aattagaata atttgtttat tgctttcgcc tataaatacg    3480
acggatcgta atttgtcgtt ttatcaaaat gtactttcat tttataataa cgctgcggac    3540
atctacattt ttgaattgaa aaaaattggt aattactctt tcttttttctc catattgacc   3600 atcatactca ttgctgatcc atgtagattt cccggacatg aagccattta caattgaata    3660
tatcctaagt aaaacctcat aggttttacg tatttcattt agggac                    3706

<210> SEQ ID NO 7
<211> LENGTH: 23
<212> TYPE: DNA
<213> ORGANISM: Artificial Sequence
<220> FEATURE:
<221> NAME/KEY: misc_feature
<223> OTHER INFORMATION: Primer

<400> SEQUENCE: 7
atgcattggc ctttgttttt gat                                              23

<210> SEQ ID NO 8
<211> LENGTH: 19
<212> TYPE: DNA
<213> ORGANISM: Artificial Sequence
<220> FEATURE:
<221> NAME/KEY: misc_feature
<223> OTHER INFORMATION: Primer

<400> SEQUENCE: 8
tgtcgtttcc cgccttcag                                                   19

<210> SEQ ID NO 9
<211> LENGTH: 26
<212> TYPE: DNA
<213> ORGANISM: Artificial Sequence
<220> FEATURE:
<221> NAME/KEY: misc_feature
<223> OTHER INFORMATION: Primer

<400> SEQUENCE: 9
cgctgcggac atctacattt ttgaat                                           26

<210> SEQ ID NO 10
<211> LENGTH: 28
<212> TYPE: DNA
<213> ORGANISM: Artificial Sequence
<220> FEATURE:
<221> NAME/KEY: misc_feature
<223> OTHER INFORMATION: Primer

<400> SEQUENCE: 10
agttaacttt ccacttatcg gggcactg                                         28

<210> SEQ ID NO 11
<211> LENGTH: 288
<212> TYPE: DNA
<213> ORGANISM: Artificial Sequence
<220> FEATURE:
<221> NAME/KEY: misc_feature
<223> OTHER INFORMATION: PCR product

<400> SEQUENCE: 11
atgcattggc ctttgttttt gatggcatca actttggagc atctgatttt gcatattcag      60
ccttttccat ggtaattctt ttacaagaat tttcattctt tcttaagtat aaacacttag     120
```

-continued

```
cttgggacaa acttctgatc ctatttctta attttttgcag gcgatggtgg ctgttatgag    180 catttttgtgt ttgatgtttc tctcttctca ttacggtttt attgggatct gggtggctct   240
aactatttac atgagcctcc gcgcgtttgc tgaaggcggg aaacgaca                 288
```

<210> SEQ ID NO 12
<211> LENGTH: 751
<212> TYPE: DNA
<213> ORGANISM: Artificial Sequence
<220> FEATURE:
<221> NAME/KEY: misc_feature
<223> OTHER INFORMATION: PCR product

<400> SEQUENCE: 12

```
cgctgcggac atctcacattt ttgaattgaa aaaaaattgg taattactct ttcttttttct    60 ccatattgac catcatactc attgctgatc catgtagatt tcccggacat gaagccattt   120
acaattgaat atatcctaag taaaacctca taggttttac gtatttcatt tagggactaa   180
aatggtttag gataattact ttagctaaca taagataata aataaataaa taaataaaaa   240
taaaatggtt gtagataaat aaggaaatca ataatgaata tgagtgtgag tgataggacg   300
ggaatgggaa acttttacac tactttaacg ctattgaacg agtatgagta tgttataaac   360
gtaaaatgtt ttatgtgtta gacaatggcc tcaagtgaaa gtgaccctat taatggagga   420
aatgcaaacc acgagtctga ggtcacgctc gaagaaatga gggcaaggat cgacgcattg   480
cgtagcgacc ctgttttttgg agatgccacg ggagatgcta gtgataaccg aatggattta   540
atgaggttga tgatgatgga gcttttacaa ggaaatcgac aaaggcctag aactgaacaa   600
gaagagtgct caaacatgtt caagaggttt tcggctcata gcccccaac ttatgatgga   660 aagccagacc ccactgagtt tgaagaatgg ctcaacggca tggaaaaatt gttcgatgcc   720
acccagtgcc ccgataagtg gaaagttaac t                                  751
```

<210> SEQ ID NO 13
<211> LENGTH: 664
<212> TYPE: DNA
<213> ORGANISM: Artificial Sequence
<220> FEATURE:
<221> NAME/KEY: misc_feature
<223> OTHER INFORMATION: PCR product

<400> SEQUENCE: 13

```
ttaattttttg caggcgatgg tggctgttat gagcattttg tgtttgatgt ttctctcttc    60
tcattacggt tttattggga tctggtggc tctaactatt tacatgagcc tccgcgcgtt   120
tgctgaaggc gggaaacgac aatctgatcc ccatcaagct tgagctcagg atttagcagc   180
attccagatt gggttcaatc aacaaggtac gagccatatc actttattca aattggtatc   240
gccaaaacca agaaggaact cccatcctca aaggtttgta aggaagaatt ctcagtccaa   300
agcctcaaca aggtcagggt acagagtctc caaaccatta gccaaaagct acaggagatc   360
aatgaagaat cttcaatcaa agtaaactac tgttccagca catgcatcat ggtcagtaag   420
tttcagaaaa agacatccac cgaagactta agttagtgg gcatctttga agtaatcctt   480
gtcaacatcg agcagctggc ttgtggggac cagacaaaaa aggaatggtg cagaattgtt   540
aggcgcacct accaaaagca tctttgcctt tattgcaaag ataaagcaga ttcctctagt   600
acaagtgggg aacaaaataa cgtggaaaag agctgtcctg cagcccact cactaatgcg   660 tatg                                                               664
```

<210> SEQ ID NO 14
<211> LENGTH: 30
<212> TYPE: DNA
<213> ORGANISM: Artificial Sequence
<220> FEATURE:
<221> NAME/KEY: misc_feature
<223> OTHER INFORMATION: Primer

<400> SEQUENCE: 14
gctctgacac aaccggtaaa tgcattggcc                              30

<210> SEQ ID NO 15
<211> LENGTH: 30
<212> TYPE: DNA
<213> ORGANISM: Artificial Sequence
<220> FEATURE:
<221> NAME/KEY: misc_feature
<223> OTHER INFORMATION: Primer

<400> SEQUENCE: 15
gacccatagt ttgattttaa gcacgacatg                              30

<210> SEQ ID NO 16
<211> LENGTH: 29
<212> TYPE: DNA
<213> ORGANISM: Artificial Sequence
<220> FEATURE:
<221> NAME/KEY: misc_feature
<223> OTHER INFORMATION: Primer

<400> SEQUENCE: 16
gcagattctg ctaacttgcg ccatcggag                               29

<210> SEQ ID NO 17
<211> LENGTH: 1042
<212> TYPE: DNA
<213> ORGANISM: Artificial Sequence
<220> FEATURE:
<221> NAME/KEY: misc_feature
<223> OTHER INFORMATION: PCR product

<400> SEQUENCE: 17
gctctgacac aaccggtaaa tgcattggcc tttgttttg atggcatcaa ctttggagca      60
tctgattttg catattcagc cttttccatg gtaattcttt tacaagaatt ttcattcttt    120
cttaagtata aacacttagc ttgggacaaa cttctgatcc tatttcttaa tttttgcagg    180
cgatggtggc tgttatgagc attttgtgtt tgatgtttct ctcttctcat tacggtttta    240
ttgggatctg ggtggctcta actatttaca tgagcctccg cgcgtttgct gaaggcggga    300
aacgacaatc tgatccccat caagcttgag ctcaggattt agcagcattc cagattgggt    360
tcaatcaaca aggtacgagc catatcactt tattcaaatt ggtatcgcca aaaccaagaa    420
ggaactccca tcctcaaagg tttgtaagga agaattctca gtccaaagcc tcaacaaggt    480
cagggtacag agtctccaaa ccattagcca aaagctacag gagatcaatg aagaatcttc    540
aatcaaagta aactactgtt ccagcacatg catcatggtc agtaagtttc agaaaaagac    600
atccaccgaa gacttaaagt tagtgggcat ctttgaaagt aatcttgtca acatcgagca    660
gctggcttgt ggggaccaga caaaaaagga atggtgcaga attgttaggc gcacctacca    720
aaagcatctt tgccttttatt gcaaagataa agcagattcc tctagtacaa gtggggaaca    780
aaataacgtg gaaagagct gtcctgacag cccactcact aatgcgtatg acgaacgcag    840
tgacgaccac aaaagaattc cctctatata agaaggcatt cattcccatt tgaaggatca    900

```
tcagatactg aaccaatcct tctagaagat ctaagcttat cgataagctt gatgtaattg    960
gaggaagatc aaaattttca atccccattc ttcgattgct tcaattgaag tttctccgat   1020
ggcgcaagtt agcagaatct gc                                            1042
```

GLYPHOSATE TOLERANT SUGAR BEET

BACKGROUND OF THE INVENTION

Field of the Invention

The invention relates to glyphosate tolerant sugar beet plants, plant material and seeds.

Sugar beet (*Beta vulgaris*) is grown as a commercial crop in many countries, with a combined harvest of over 240 million metric tons.

N-phosphonomethyl-glycine, commonly referred to as glyphosate, is a broad spectrum herbicide, which is widely used due to its high efficiency, biodegradability, and low toxicity to animals and humans. Glyphosate inhibits the shikimic acid pathway which leads to the biosynthesis of aromatic compounds including amino acids and vitamins. Specifically, glyphosate inhibits the conversion of phosphoenolpyruvic acid and 3-phosphoshikimic acid to 5-enolpyruvyl-3-phosphoshikimic acid by inhibiting the enzyme 5-enolpyruvyl-3-phosphoshikimic acid synthase (EPSP synthase or EPSPS). When conventional plants are treated with glyphosate, the plants cannot produce the aromatic amino acids (e.g. phenylalanine and tyrosine) needed to grow and survive. EPSPS is present in all plants, bacteria, and fungi. It is not present in animals, which do not synthesize their own aromatic amino acids. Because the aromatic amino acid biosynthetic pathway is not present in mammals, birds or aquatic life forms, glyphosate has little if any toxicity for these organisms. The EPSPS enzyme is naturally present in foods derived from plant and microbial sources.

Glyphosate is the active ingredient in herbicides such as Roundup®, produced by Monsanto Company, USA. Typically, it is formulated as a water-soluble salt such as an ammonium, alkylamine, alkali metal or trimethylsulfonium salt. One of the most common formulations is the isopropylamine salt of glyphosate, which is the form employed in Roundup® herbicide.

It has been shown that glyphosate tolerant plants can be produced by inserting into the genome of the plant the capacity to produce an EPSP synthase which is glyphosate tolerant, e.g. the CP4-EPSPS from Agrobacterium sp. strain CP4.

DESCRIPTION OF THE RELATED ART

A glyphosate tolerant sugar beet plant may be produced by Agrobacterium mediated transformation, introducing a gene coding for a glyphosate tolerant EPSPS such as CP4-EPSPS into the plant's genome. Such a sugar beet plant, expressing CP4-EPSPS, has been described in WO 99/23232. However, sugar beet plants grown from cells transformed with the gene for CP4-EPSPS in this manner, differ widely in their characteristics, due to the fact that the gene is inserted at a random position in the plant genome. The insertion of a particular transgene into a specific location on a chromosome is often referred to as an "event". The term "event" is also used to differentiate genetically engineered crop varieties. Desirable events are very rare. By far the most events are discarded because the transgene inserted into a plant gene important for growth, causing the gene to be disrupted and not expressed, or the transgene inserted into a portion of the chromosome that does not allow for expression of the transgene or expression that is too low. For this reason, it is necessary to screen a large number of events in order to identify an event characterized by sufficient expression of the introduced gene. This procedure is very time and cost consuming, and it is in no way guaranteed that a plant with satisfactory properties may be found.

SUMMARY OF THE INVENTION

Therefore, it is the object of the present invention to provide a sugar beet plant that shows a high level of tolerance against glyphosate, but has no disadvantages with respect to other important agronomic properties such as growth, yield, quality, pathogen resistance etc.

The glyphosate tolerant sugar beet plant according to the invention is characterized in that a) the sugar beet plant is obtained from seed deposited with the NCIMB, Aberdeen (Scotland, U.K.) and having the accession number NCIMB 41158 or NCIMB 41159, and/or b) a DNA fragment of between 630-700 bp, preferably 664 bp, can be amplified from the genomic DNA of said sugar beet plant, parts or seeds thereof, using polymerase chain reaction with a first primer having the nucleotide sequence of SEQ ID NO: 1 and a second primer having the nucleotide sequence of SEQ ID NO: 2, and/or c) a DNA fragment of 3500-3900, preferably 3706 bp, can be amplified from the genomic DNA of said sugar beet plant, parts or seeds thereof, using polymerase chain reaction with a first primer having the nucleotide sequence of SEQ ID NO: 3 and a second primer having the nucleotide sequence of SEQ ID NO: 4, and/or d) a DNA fragment of 270-300 bp, preferably 288 bp, can be amplified from the genomic DNA of said sugar beet plant, parts or seeds thereof, using polymerase chain reaction with a first primer having the nucleotide sequence of SEQ ID NO: 7 and a second primer having the nucleotide sequence of SEQ ID NO: 8, and/or e) a DNA fragment of 710-790 bp, preferably 751 bp, can be amplified from the genomic DNA of said sugar beet plant, parts or seeds thereof, using polymerase chain reaction with a first primer having the nucleotide sequence of SEQ ID NO: 9 and a second primer having the nucleotide sequence of SEQ ID NO: 10, and/or f) a DNA fragment of 990-1100 bp, preferably 1042 bp, can be amplified from the genomic DNA of said sugar beet plant, parts or seeds thereof, using polymerase chain reaction with a first primer having the nucleotide sequence of SEQ ID NO: 14 and a second primer having the nucleotide sequence of SEQ ID NO: 16.

Polymerase chain reaction (PCR) is a well-known standard method used to amplify nucleic acid molecules (see for example U.S. Pat. No. 4,683,202).

The sugar beet plant according to the invention (in the following referred to as "event H7-1") shows a high tolerance to glyphosate herbicide. In addition, growth characteristics and other important agronomic properties of event H7-1 are not affected by the transformation process. Event H7-1 expresses a high level of the Agrobacterium-CP4-EPSPS-gene, which is stably incorporated within the plant genome, and which confers glyphosate tolerance to the plant. The plant has been produced by Agrobacterium mediated transformation technology using the binary vector PV-BVGT08. This vector contained between the left and right border region the following sequences: a coding region composed of a chloroplast transit peptide coding sequence from the *Arabidopsis thaliana* EPSPS (designated ctp2) joined to the CP4-EPSPS coding sequence and under the regulation of the Figwort mosaic virus promoter (pFMV) and the E9-3' transcriptional termination sequence from *Pisum sativum*.

In a preferred embodiment of the invention the 3706 bp, 664 bp, 288 bp, 751 bp and 1042 bp DNA fragments show at least 95%, preferably at least 99%, more preferably at least 99,9%, identity with the nucleotide sequences of SEQ ID NO: 6, SEQ ID NO: 13, SEQ ID NO: 11, SEQ ID NO: 12 or SEQ ID NO: 17, respectively. 95% identity, for example, means that 95% of the nucleotides of a given sequence are identical with the compared sequence. For this purpose, the sequences may be aligned and compared using the BLAST programme. Most preferably, the 3706 bp DNA fragment has the nucleotide sequence of SEQ ID NO: 6, the 664 bp DNA fragment has the nucleotide sequence of SEQ ID NO: 13, the 288 bp DNA fragment has the nucleotide sequence of SEQ ID NO: 11, the 751 bp DNA fragment has the nucleotide sequence of SEQ ID NO: 12, and/or the 1042 15p DNA fragment has the nucleotide sequence of SEQ ID NO: 17.

The present invention also refers to seed deposited with the NCIMB, Aberdeen (Scotland, U.K.), and having the accession number NCIMB 41158 or NCIMB 41159. Such seed can be used to obtain a glyphosate tolerant sugar beet plant. The seed can be sawn and the growing plant will be glyphosate tolerant.

The invention also relates to a cell, tissue or part of a glyphosate tolerant sugar beet plant.

Another aspect of the present invention is a method for the identification of a glyphosate tolerant sugar beet plant, characterized in that the method comprises the step(s) of a) amplifying a DNA fragment of between 630-700 bp, preferably 664 bp, from the genomic DNA of said sugar beet plant, parts or seeds thereof, using polymerase chain reaction with a first primer having the nucleotide sequence of SEQ ID NO: 1 and a second primer having the nucleotide sequence of SEQ ID NO: 2, and/or b) amplifying a DNA fragment of 3500-3900, preferably 3706 bp, from the genomic DNA of said sugar beet plant, parts or seeds thereof, using polymerase chain reaction with a first primer having the nucleotide sequence of SEQ ID NO: 3 and a second primer having the nucleotide sequence of SEQ ID NO: 4, and/or c) amplifying a DNA fragment of 270-300 bp, preferably 288 bp, from the genomic DNA of said sugar beet plant, parts or seeds thereof, using polymerase chain reaction with a first primer having the nucleotide sequence of SEQ ID NO: 7 and a second primer having the nucleotide sequence of SEQ ID NO: 8, and/or d) amplifying a DNA fragment of 710-790 bp, preferably 751 bp, from the genomic DNA of said sugar beet plant, parts or seeds thereof, using polymerase chain reaction with a first primer having the nucleotide sequence of SEQ ID NO: 9 and a second primer having the nucleotide sequence of SEQ ID NO: 10, and/or e) amplifying a DNA fragment of 990-1100 bp, preferably 1042 bp, from the genomic DNA of said sugar beet plant, parts or seeds thereof, using polymerase chain reaction with a first primer having the nucleotide sequence of SEQ ID NO: 14 and a second primer having the nucleotide sequence of SEQ ID NO: 16.

The method allows easy detection of a transgenic glyphosate tolerant sugar beet plant with standard molecular biology techniques.

The invention further relates to a test kit for the identification of a transgenic glyphosate tolerant sugar beet plant or its cells, tissue or parts. The kit comprises at least one primer pair with a first and a second primer for polymerase chain reaction, which allow to identify specifically event H7-1, its cells, tissue or parts.

Preferably, the first primer has the nucleotide sequence of SEQ ID NO: 1 or SEQ ID NO: 7 or SEQ ID NO: 9 or SEQ ID NO: 14, and the second primer has the nucleotide sequence of SEQ ID NO: 2 or SEQ ID NO: 8 or SEQ ID NO: 10 or SEQ ID NO: 16.

According to a further embodiment of the present invention, the first and second primer each recognize a nucleotide sequence which forms part of the nucleotide sequence of SEQ ID NO: 5.

BRIEF DESCRIPTION OF THE DRAWINGS

The following figures serve to elucidate the invention.
It shows:

FIG. 11 Comparison between the PCR fragments and the PV-BVGT08 sequences on the left border region.

DETAILED DESCRIPTION OF THE INVENTION

Figure 1:
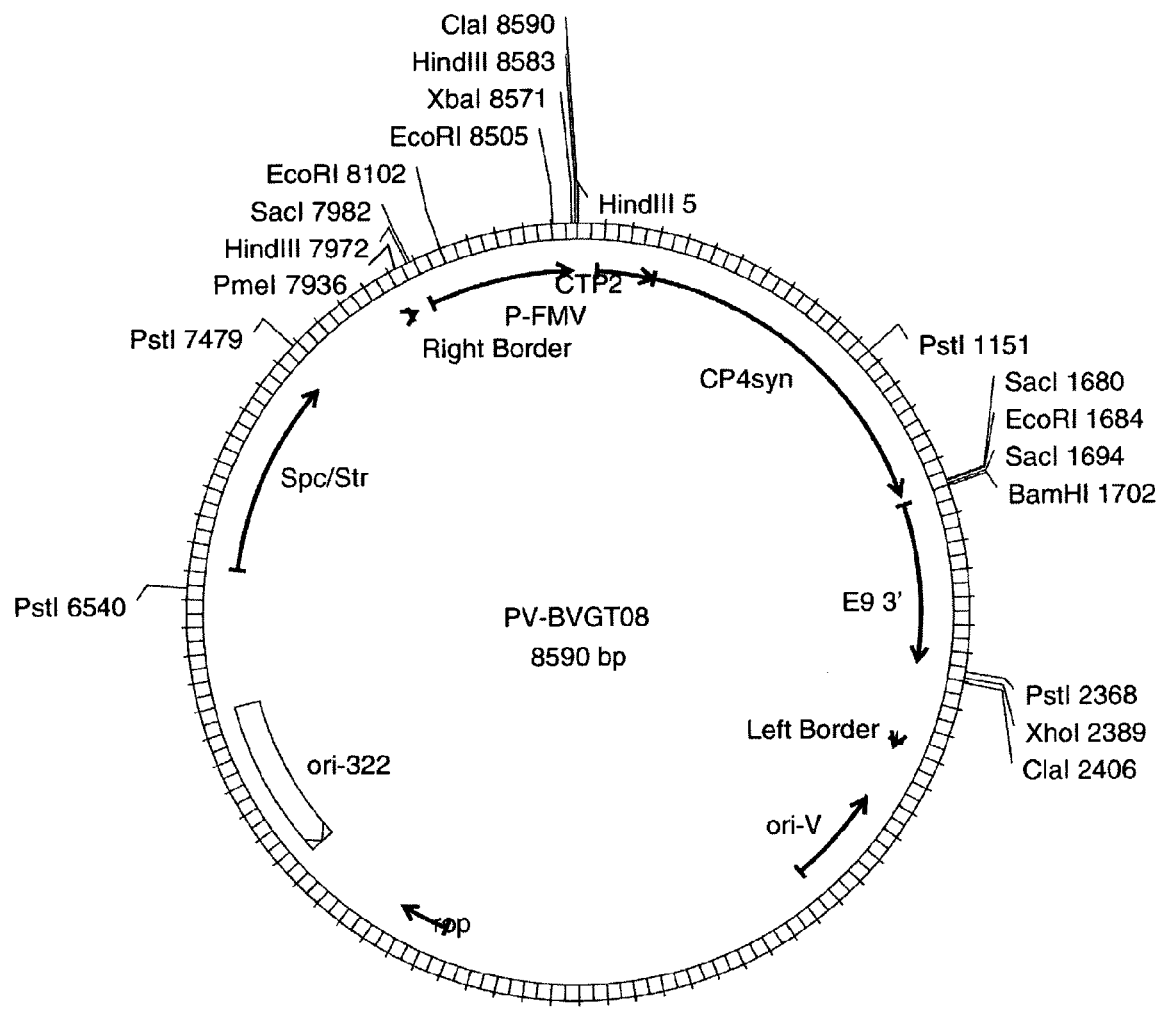
FIG. 1 Map of the binary vector PV-BVGT08

The invention is further defined, by way of illustration only, by reference to the following examples.

A list of abbreviations used is given below:

| | |
|---|---|
| ~ | approximately |
| ° C. | degree Celsius |
| bidest | double destillated sterile water |
| bp | base pair(s) |
| CTAB | cetyltrimethylammonium bromide |
| DNA | deoxyribonucleic acid |
| E. coli | Escherichia coli |
| EDTA | ethylendiaminetetraacetic acid |
| FIG. | Figure |
| h | hour |
| HCl | hydrochloric acid |
| kb | kilobase pair |
| kg | kilogram |
| M, mM, | molar, millimolar |
| min | minutes |
| Na$_2$HPO$_4$/NaH$_2$PO$_4$ | sodium phosphate |
| NaCl | sodium chloride |
| NaOH | sodium hydroxide |
| nt | nucleotide |
| PCR | polymerase chain reaction |
| pmol | picomole |
| RNase | ribonucleic acid nuclease |
| rpm | revolutions per minute |
| RR | Roundup Ready ® |
| RT | room temperature |
| SDS | sodium dodecyl sulfate |
| sec | second |
| SEVAG | Chloroform:Isoamyl alcohol (24:1) |
| SSC | standard saline citrate |
| TE | Tris-EDTA buffer |
| TRIS | tris(hydroxymethyl)-aminomethane |

EXAMPLE 1

Identification of Event H7-1

Sugar beet (*Beta vulgaris*) genotype 3S0057 has been genetically modified to express a CP4-5-Enol-Pyruvyl-Shikimate-3-Phosphate Synthase or CP4-EPSPS, which confers tolerance to the herbicide glyphosate and is also used as a selectable marker. This transgenic line was produced by *Agrobacterium-tumefaciens* mediated transformation technology using the binary vector PV-BVGT08. The T-DNA of the vector used for sugar beet transformation contained between the left and the right border region the following sequences: a coding region composed of a chloroplast transit peptide coding sequence from the *Arabidopsis thaliana* EPSPS (designated ctp2) joined to the CP4-EPSPS coding sequence and under the regulation of the 35S Figwort mosaic virus promoter (pFMV) and the *Pisum sativum* rbcS-E9-gene 3'-transcriptional termination sequence.

The following methods were used:

I. DNA Extraction:

Method 1:

Fresh leaf or other tissue was collected (20 to 100 mg in a 1.5 ml tube) and 400 μl extraction buffer (see below) were added. The tissue was ground with a small pestle. The mixture was vortexed for 5 sec and incubated 30 min to 60 min at room temperature. A centrifugation step at 13,000 rpm for 1 min followed. The supernatant containing the DNA was poured into a new 1.5 ml tube and mixed with 320 μl isopropanol. The mixture was incubated at room temperature for 2 min. A DNA precipitate is formed after the addition of ethanol. After centrifugation at 13,000 rpm for 5 min the ethanol was decanted. The sample was allowed to air dry. The pellet was redissolved in 400 μl H$_2$O or TE-buffer (see below).

| Extraction buffer (100 ml): | |
|---|---|
| 20 ml | 1 M Tris (pH 7.5) |
| 5 ml | 5 M NaCl |
| 5 ml | 0.5 M EDTA |
| 2.5 ml | 20% SDS |
| 67.5 ml | H$_2$O |

TE-buffer:

10 mM Tris-HCl (pH 8.0)

1 mM EDTA

Method 2:

Fresh plant material (20 to 100 mg) was collected in a 1.5 ml Eppendorf tube and 500 μl CTAB buffer (65° C.) (see below) were added. The mixture was incubated 1 to 1.5 h at 65° C., and subsequently centrifuged for 5 sec. 5 μl RNase A (10 mg/ml), were added. The mixture was incubated 30 min at 37° C. and subsequently centrifuged for 5 sec. 200 μl SEVAG were added. After mixing and centrifugation at 13,000 rpm for 10 min the supernatant was transferred to a new 1.5 ml tube. 1 volume isopropanol (about 400 μl) was mixed carefully with the supernatant. A centrifugation step at 13,000 rpm for 10 min followed. 600 μl 70% ethanol were added. The pellet was washed by inverting the tube several times. Again, the mixture was centrifuged at 13,000 rpm for 2 min. The ethanol was carefully discarded. The tube was inverted and drained on clean paper. The sample was allowed to air dry for 15 min. The pellet was redissolved in 50 µl H$_2$O (see below).

CTAB buffer:
1.4 M NaCl
20 mM EDTA
100 mM Tris-HCl
2% (w/v) CTAB

SEVAG:
Chloroform:Isoamylalcohol (24:1)

RNase-buffer:
10 mM Tris, 15 mM NaCl, pH 7.5

RNase A:
10 mg RNase/ml RNase-buffer
(5 ml bidest+50 mg RNase A, Aliquots in 1.5 ml tubes, boil tubes 30 min at 100° C., storage at −20° C.)

Normally, Method 1 was used. With this method it is possible to extract a high number of DNA samples per day and the DNA quality is acceptable. Method 2 was used, when the leaf material was older or if there were problems with the DNA quality. Method 2 is more complex, requires more time, and gives a lower DNA yield, but of higher quality.

Normally, quantitation of DNA is not performed, and typically in a PCR reaction 0.5 to 1 µl of the extracted DNA solution is used.

PCR reaction:

For the PCR reaction, a 10× buffer mix of buffer+dNTP's was prepared. The procedure is as follows:

| Stock solution | volume | 10× buffer conc. | final PCR reaction conc. |
|---|---|---|---|
| 1 M Tris-HCl, pH 8.3 | 100 µl | 0.1 M | 10 mM Tris-HCl, pH 8.3 |
| 1 M KCl | 500 µl | 0.5 M | 50 mM KCl |
| 100 mM dATP | 20 µl | 2 mM | 0.2 mM dATP |
| 100 mM dCTP | 20 µl | 2 mM | 0.2 mM dCTP |
| 100 mM dTTP | 20 µl | 2 mM | 0.2 mM dTTP |
| 100 mM dGTP | 20 µl | 2 mM | 0.2 mM dGTP |
| 100 mM MgCl$_2$ | 150 µl | 15 mM | 1.5 mM MgCl$_2$ |
| HPLC water | 170 µl | | |
| | 1000 µl total | | |

| PCR reaction (25 µl): | |
|---|---|
| DNA | 0.5 µl |
| Primer 1 | 1 µl (20 pmol) |
| Primer 2 | 1 µl (20 pmol) |
| Taq polymerase 1 | 0.2 µl (1 U, from Oncor Appligene S.A., Heidelberg, Germany) |
| Buffer 10 × conc. | 2.5 µl |
| Water | 18.8 µl |

III. Identification of H7-1 by PCR

The Identification of H7-1 was performed by PCR using event specific primers:

Upper Primer (SEQ ID NO: 1):
H7-207U30: 5' TTA ATT TTT GCA GGC GAT GGT GGC TGT TAT 3'

Lower Primer (SEQ ID NO: 2):
H7-841L30: 5' CAT ACG CAT TAG TGA GTG GGC TGT CAG GAC 3'

The upper primer is located outside of the insert, and is part of the sugar beet genomic DNA. The lower primer is located within the inserted CP4-EPSPS gene. PCR conditions:

| PCR conditions: | |
|---|---|
| 94° C. 4 min | STEP 1 |
| 95° C. 30 sec | STEP 2a |
| 55° C. 30 sec | STEP 2b |
| 72° C. 2 min | STEP 2c |
| 72° C. 5 min | STEP 3 |
| 4° C. over night | STEP 4 |
| | reaction complete |

Steps 2a-c were repeated 34 times.

Figure 2:
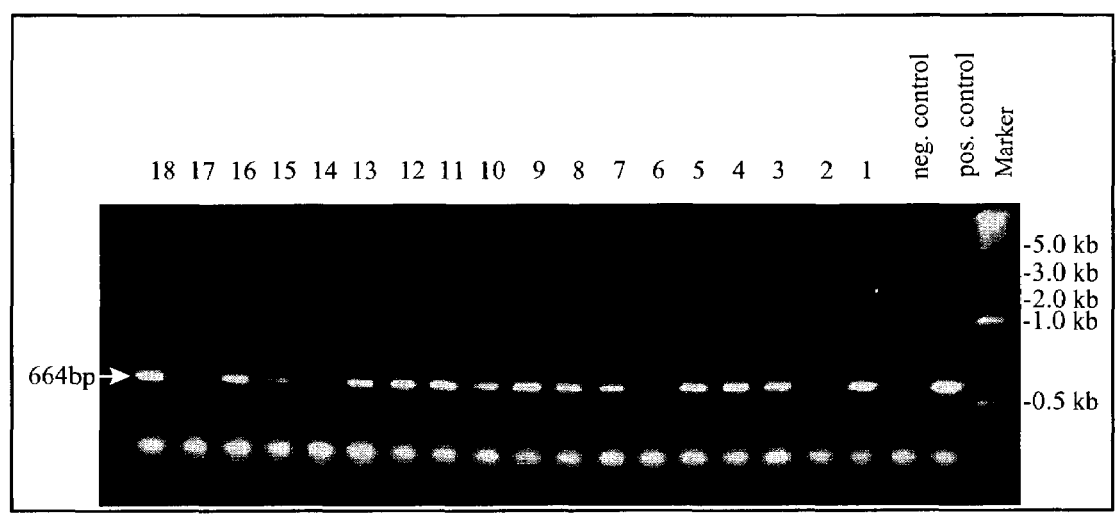
FIG. 2 Identification of H7-1 by PCR analysis. DNA samples from 18 plants have been analyzed. Neg. control=DNA from non-transformed sugarbeet; pos. control=DNA from H7-1 original transformant.

The expected PCR product is a DNA fragment of 664 bp (SEQ ID NO: 13, see FIG. 2).

IV. Identification of H7-1 by Multiplex-PCR

For the discrimination of non-transgenic and transgenic plants, whether homozygous or hemi/heterozygous, a Multiplex-PCR with three different primers was performed. Following primers were used:

H72 (SEQ ID NO: 14): 5' GCTCTGACACAACCGGTAAATGCATT GGCC 3'

H7S2 (SEQ ID NO: 15): 5' GACCCATAGTTTGATTTTAAGCACGA CATG 3'

H7R2 (SEQ ID NO: 16): 5' GCAGATTCTGCTAACTTGCGCCATCG GAG 3'

| PCR conditions: | |
|---|---|
| 94° C. 2 min | STEP 1 |
| 94° C. 1 sec | STEP 2a |
| 60° C. 45 sec | STEP 2b |
| 72° C. 90 sec | STEP 2c |
| 72° C. 5 min | STEP 3 |
| 4° C. over night | STEP 4 |
| | reaction complete |

Steps 2a-c were repeated 34 times.

Figure 3:
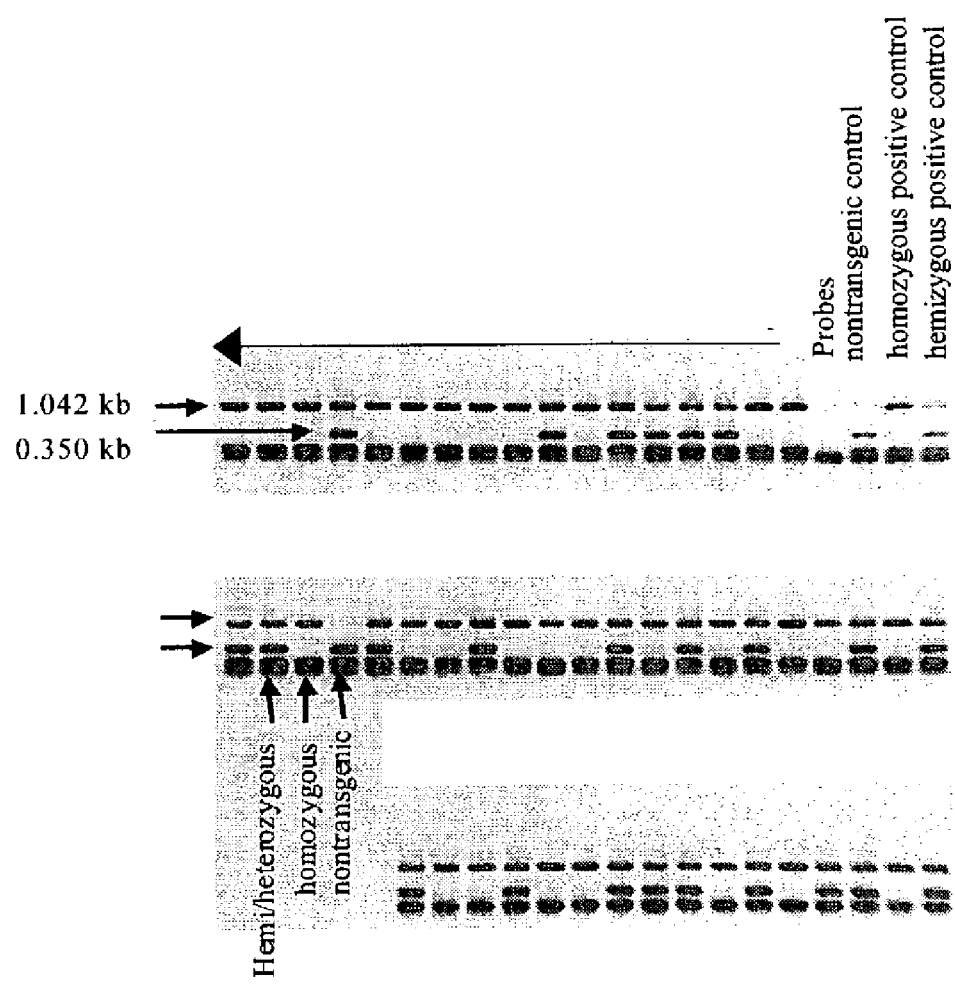
FIG. 3 Identification of event H7-1 by Multiplex-PCR and discrimination between transgenic event H7-1 and non-transgenic plants. DNA samples from 54 plants have been analyzed.

Non-transgenic plants show only one PCR fragment of about 350 bp. Homozygous transgenic plants show one fragment of about 1.042 kb. Heterozygous plants show both fragments (see FIG. 3).

EXAMPLE 2

Characterization of Event H7-1

Molecular analysis was performed to characterize the integrated DNA present in the event H7-1. Specifically, the insert number (number of integration sites within the sugar beet genome), the copy number (the number of DNA fragments within one locus), the integrity of the inserted coding region and its regulatory elements, the pFMV promoter and E9-3' transcriptional termination sequence, the absence of backbone sequences of the vector used for transformation and the stable inheritance of the insert were determined. Further, the sequences flanking the DNA insert were identified.

The inserted DNA of the sugar beet transformation event H7-1 was characterized by using Southern blot, PCR and Inverse-PCR techniques. Positive and negative controls (PV-BVGT08, non-transgenic plant DNA) were included and were treated in the same manner as the test substance (H7-1).

DNA was isolated from batch number 74903H of event H7-1 plants grown in 1997. DNA was also isolated from the original transformant H7-1/3S0057 (=6401VH) in 1995 and from three additional progenies produced in 1996, 1997, and 1998. (H7-1/64801H, H7-1/74922H, and H7-1/83002S).

The non-transgenic sugar beet line 3S0057 served as control. In addition, sugar beet lines 5R7150, 8K1180, and 6S0085 were used as a negative control. Those lines are common non-transgenic lines used for breeding conventional sugar beet.

Reference substances correspond to the plasmid PV-BVGT08 used for the transformation. The plasmid DNA and DNA from the control sugar beet line were mixed together, digested with restriction enzyme and separated by electrophoresis on agarose gels in parallel to the test substances. The plasmid served as a size marker for the expected fragment and as a positive hybridization control. The plasmid DNA was mixed with the genomic plant DNA at a concentration representing less than 1 copy of the element being analysed to demonstrate the sensitivity of the Southern blot method (~10 µg genomic DNA and ~28 pg PV-BVGT08 DNA). For size estimations the molecular size marker RAOUL™ (ONCOR/Appligene, catalog #160673) was used.

DNA Isolation:

Plant tissue (1 to 3 g wet weight) from batch number 74903H of event H7-1 was ground in liquid nitrogen to a fine powder using a mortar and pestle. The powder was transferred to a 50 ml Oakridge tube, and 7.5 ml of preheated (60° C.) CTAB buffer (2% CTAB, 100 mM Tris-HCl, 20 mM EDTA pH 8.0, 1.4 M NaCl and 0.2% mercapto-ethanol) was added. The samples were incubated at 65° C. for approximately 30 min with intermittent mixing. An equal volume (8 ml) of a mixture of RT chloroform:isoamylalcohol (24:1 v/v) was added to the samples. The suspension was mixed by inversion, and the two phases were separated by centrifugation (10 min, 9000 rpm). The aqueous phase was transferred to a new 50 ml Oakridge tube following the precipitation of the DNA by adding 5 ml isopropanol. The DNA was pelleted by centrifugation (2 min, 9000 rpm) and the supernatant was removed. The precipitated DNA was incubated with a wash solution of 76% ethanol and 10 mM ammoniumacetate for about 20 min. After centrifugation and decanting of the supernatant the DNA was vacuum dried and redissolved in TE, pH 8.0 at 4° C. overnight.

As an alternative method, DNA was isolated by DNeasy Plant Maxi Kit from Qiagen (Düsseldorf, Germany, catalog #68163). DNA isolation was carried out according to the manufacturer's manual.

As an additional alternative method, DNA was isolated by DNeasy Plant Mini Kit from Qiagen (Düsseldorf, Germany, catalog #69103). DNA isolation was carried out according to the manufacturer's manual.

DNA Quantification and Restriction Enzyme Digestion:

DNA quantification was performed using a LKB Biochrom UV/visible spectrophotometer (Amersham Pharmacia, Freiburg, Germany) or, alternatively, DNA quantification was done after agarose gel electrophoresis by scanning the DNA with the RFLPscan program (MWG-Biotech, Ebersberg, Germany). As a calibration standard the High DNA Mass Ladder from Gibco/Life Technologies (Karlsruhe, Germany) (catalog # 10496-016) was used. Restriction enzymes were purchased either from Boehringer Mannheim (Mannheim, Germany), Stratagene (Amsterdam, Netherlands) or New England Biolabs (Frankfurt, Germany) and used according to the manufacturer's manual.

DNA Probe Preparation:

PV-BVGT08 DNA was isolated from *E. coli* cultures. Probe templates homologous to the CP4-EPSPS coding region, the 35S-promoter, the E9-3'-polyadenylation region, the $^{35}$S-ctp2-CP4-EPSPS-E9-3'-cassette, and the backbone regions were prepared by digests with the corresponding restriction enzymes following a separation by agarose gel electrophoresis or by polymerase chain reaction (PCR). The products were purified using the Gene Clean II Kit of BIO 101 (La Jolla, Calif.). Labelling of the probes (25 pg) with 32P-dCTP or 32P-dATP was achieved making use of the Megaprime™ DNA labelling system of Amersham-Pharmacia Biotech Europe (Freiburg, Germany).

Southern Blot Analyses:

The samples of DNA treated with restriction enzymes were separated by agarose gel electrophoresis for ~15 hours at ~35 volts. After photographing the gel, the DNA was depurinated by soaking the gel for 15 min in a 0.25 M HCl-solution, denatured by incubating the gel for 30 min in a denaturing solution of 0.5 M NaOH, 1.5 M NaCl with constant gentle agitation and finally neutralized by soaking for 2 hours in several volumes of a solution of 2 M NaCl and 1 M Tris-HCl, pH 5.5. The DNAs from the agarose gels were transferred to Hybond-N™ nylon membranes (Amersham Pharmacia Biotech Europe, Freiburg, Germany) using a PosiBlot Pressure Blotter from Stratagene according to manufacturers protocol. After soaking the filter for 15 min in 2×SSPE (20×SSPE: 3.6 M NaCl, 20 mM EDTA, 0.2 M $NaH_2PO_4/Na_2HPO_4$ pH 7.4) the DNA was fixed to the membrane by illumination with UV-light (Transilluminator Pharmacia, Freiburg, Germany) for 0.1 min and by baking for 1 hour at 80° C. in a vacuum oven. The blots were prehybridized for 4 hours in an aqueous solution of 50% formamide, 5×SSC, 0.1% laurylsarcosine, 0.02% SDS and 2% blocking reagent (Boehringer Mannheim, Germany, catalog # 1096176). Hybridisation with the radiolabelled probe was done in fresh prehybridization solution for 16-18 hours at 42° C. After hybridisation membranes were washed for 5 min in 2×SSC at 42° C., for 20 min in 2×SSC, 1% SDS at 65° C. and for two 15 min periods in 0.2×SSC, 0.1% SDS at 68° C. Autoradiographic images of the blot were obtained by exposing the blots using Kodak Biomax MST™ film in conjunction with Kodak Biomax MS™ intensifying screens.

Identification of 5' and 3' Genomic Flanking Sequences:

The transgene-to-plant genomic DNA junctions were identified by using the Inverse-PCR technique. Genomic DNA was purified as described above. Approximately 1 µg of the DNA was digested in separate reactions by the restriction nucleases TaqI, AluI, NdeIII or RsaI. The digested DNA-fragments were religated by T4-ligase over night, followed by the PCR reaction. The various inverse-primer combinations were obtained using the primer analysis software OLIGO® from NBI (National Biosciences, Inc., Plymouth, Mich.).

Fragments resulting from this Inverse-PCR amplification were separated by gel electrophoresis, excised from the gel and purified using the Gene Clean II™ kit. The purified fragments were cloned into the vector pCR®2.1 by using the TOPO™TA cloning® Kit from Invitrogen (Groningen, Netherlands). The inserts were submitted for sequencing by MWG-Biotech (Ebersberg, Germany). Analysis of the resulting sequence data were performed using Mac Molly® Tetra DNA analysis software (Soft Gene GmbH, Bochold, Germany).

PCR Analysis:

Genomic DNA was prepared with the Plant DNAeasy Plant Mini Kit (Qiagen, Düsseldorf, Germany) according to the manufacturer's instructions. Approximately 50 ng of genomic DNA were used for PCR. The reactions were subjected to 95° C. for 30 sec, 55° C. for 30 sec, and 72° C. for 2 min for 35 cycles. PCR was done in a PTC200 cycler (Biozym, Oldendorf, Germany). PCR products were analysed by agarose gel electrophoresis.

1. Insert Number:

The insert number, the number of integration sites of transgenic DNA into the sugar beet genome, was evaluated for H7-1. In order to determine the insert number, the genomic DNA was digested with the restriction enzymes HindIII, XbaI, and BamHI. As a negative control DNA from a non transformed control plant, representing the same genetic background, was digested with Hind III. As a positive control transformation vector DNA (PV-BVGT08) was used.

Figure 4:
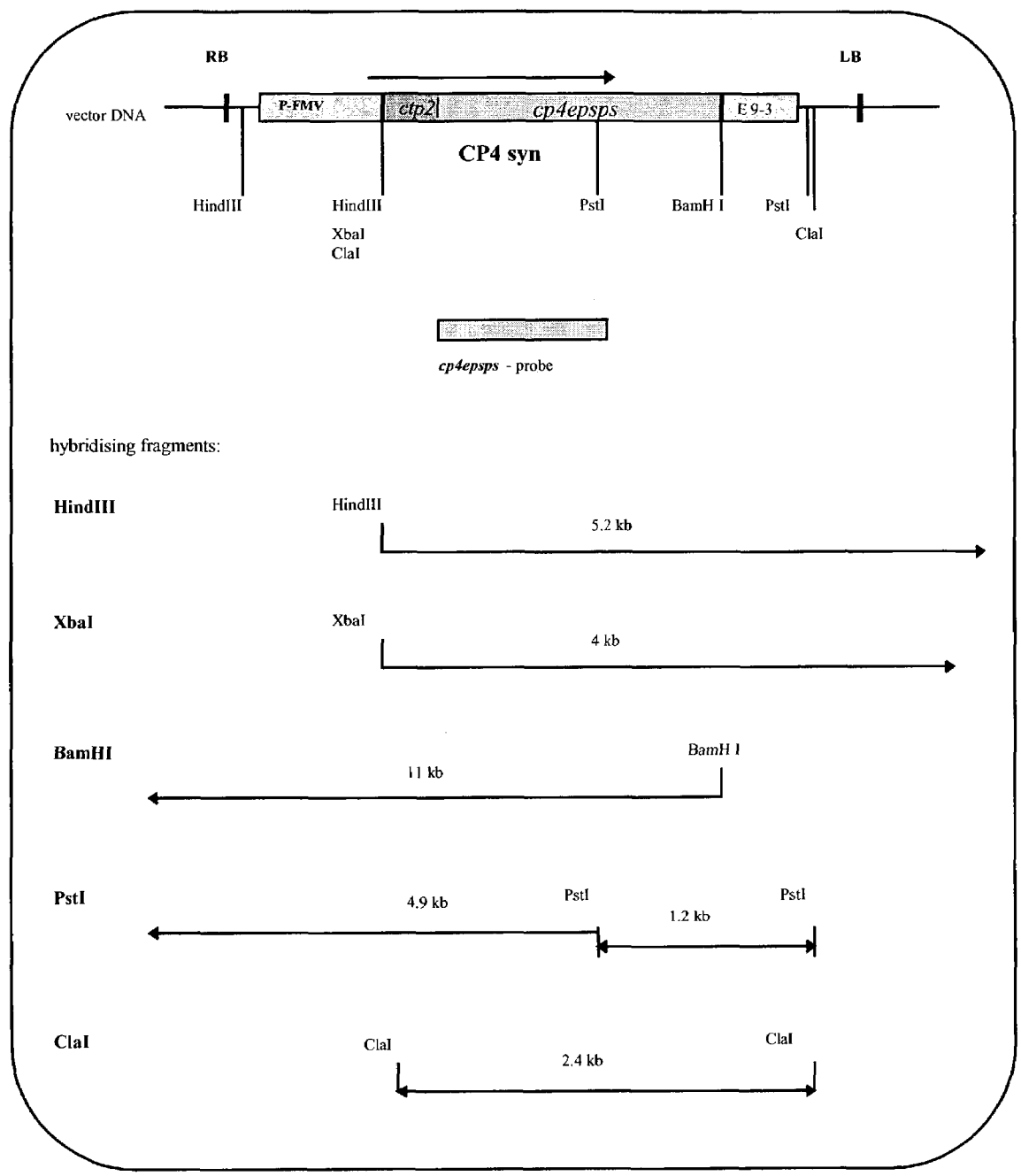
FIG. 4 The pFMV-ctp2-CP4-EPSPS-E9-3'-insert with cleavage sites of restriction enzymes HindIII, XbaI, ClaI, PstI, and BamHI.
Figure 5:
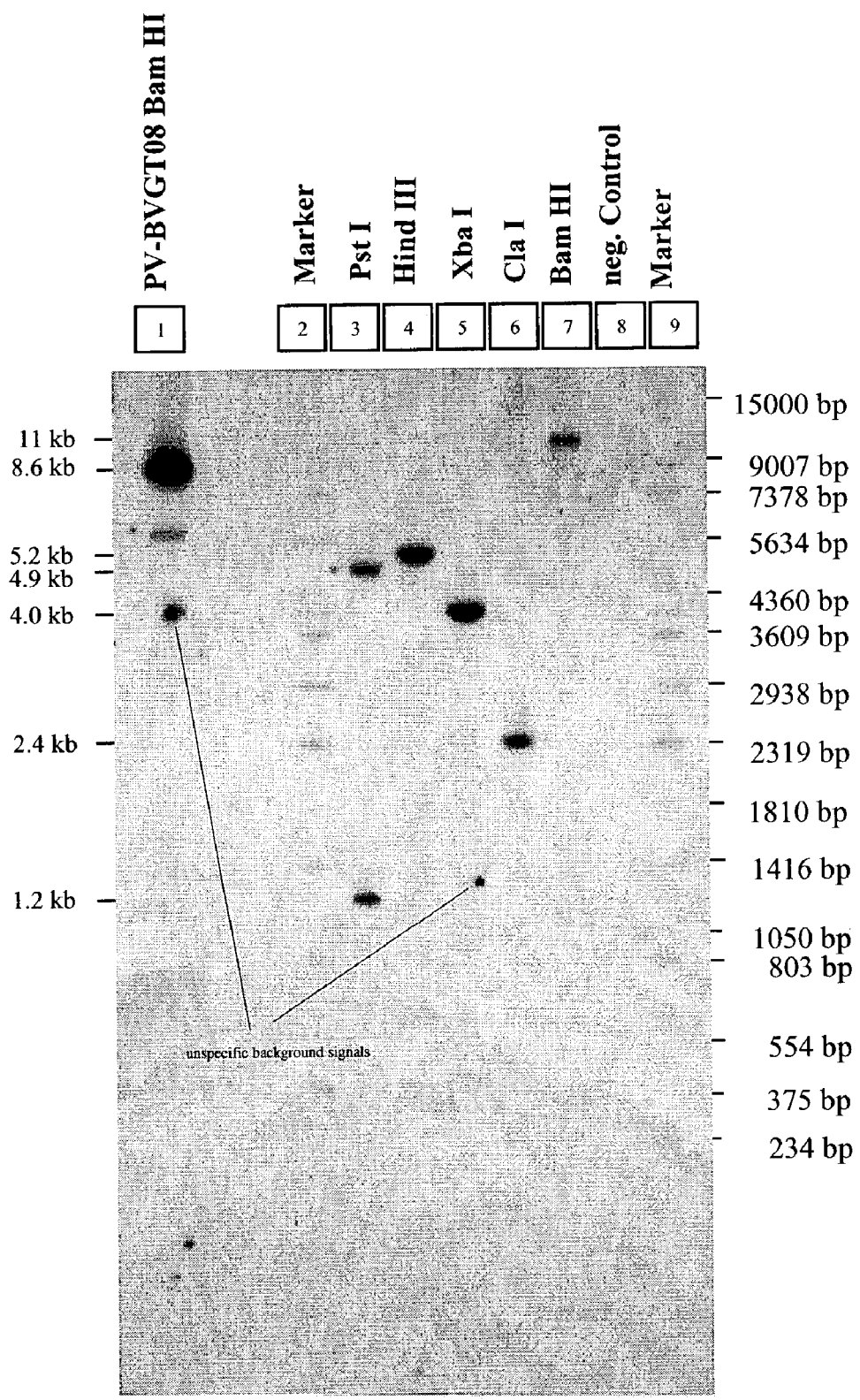
FIG. 5 Insert/copy number analysis of event H7-1. For the Southern blot analysis 10 µg of H7-1 genomic DNA were digested with PstI, HindIII, XbaI, ClaI and BamHI (lane 3 to 7). Non-transformed genomic DNA as a negative control was digested with BamHI (lane 8). Plasmid PV-BVGT08 as a positive control was digested by BamHI. Lanes 2 and 9 represent size markers. The blot was probed with a $^{32}$P-labelled CP4-EPSPS coding region. The probe is an internal sequence of the CP4-EPSPS gene covering basepairs 447-1555.

XbaI and BamHI cleave only once in PV-BVGT08 and do not cleave inside the labelled CP4-EPSPS probe used (see FIG. 4). HindIII cleaves three times in PV-BVGT08, but all three sites are located outside of the probe and on the same side, 5', relative to the probe. Thus, each enzyme should release a single DNA fragment that would hybridize to the CP4-EPSPS probe, and would contain a part of the inserted DNA and adjacent plant genomic DNA. The number of fragments detected indicates the number of inserts present in the event. The results are shown in FIG. 5.

After digestion with the enzymes HindIII, XbaI, or BamHI only a single hybridization fragment was found, respectively. The fragments of 5.2 kb from the HindIII digest (lane 4), 4 kb from the XbaI digest (lane 5) and approximately 11 kb from the BamHI digest (lane 7) showed that the transformant H7-1 represents a single integration event (FIG. 4). The strong signal in lane 1 represents the linearized PV-BVGT08 plasmid. Additional faint signals refer to small amounts of undigested PV-BVGT08 or to unspecific hybridisation background signals.

2. Copy Number

Theoretically, one integration site could consist of more than one copy of the inserted DNA. But due to the fragment sizes of the restriction analysis shown above, this was not possible. If there was more than one copy of the inserted DNA present in H7-1, additional fragments would be detected. This was proved also by a digest with the restriction enzyme PstI. PstI cleaves twice within the left and the right border sequences. One of the restriction sites is within the CP4-EPSPS coding region, so after digestion one would expect two hybridizing fragments with the CP4-EPSPS probe. One of the expected fragments corresponds to the internal fragment of about 1.2 kb. The second fragment should be a border fragment. Again, if there was more than one copy, additional fragments should be detectable. But the results show that PstI cuts the DNA as expected. The internal fragment of 1.2 kb and only one additional fragment of about 4.9 kb were detected (FIG. 5: lane 3, FIG. 4).

As an additional internal control the DNA was cleaved with ClaI (FIG. 5: lane 6, FIG. 4). As expected, a single fragment of 2.4 kb hybridized, since ClaI cleaves twice but outside left and right hand of the used CP4-EPSPS fragment. This result is also a proof of the intactness of the integrated DNA fragment and is in agreement with the results given in the following.

The hybridization of the plasmid PV-BVGT08 with the CP4-EPSPS fragment results in a 8.6 kb signal (lane 1) as expected (PV-BVGT08=8590 bp). A second smaller very faint band is due to the incomplete restriction of PV-BVGT08.

In summary the experiments show that the transformed sugar beet line H7-1 contains a single copy integration of the T-DNA of PV-BVGT08 in the plant genome.

3. Coding Region Intactness

The integrity of the CP4-EPSPS gene cassette, with respect to the individual elements (P-FMV promoter, ctp2-CP4-EPSPS coding region, and E9 3' non-translated region), was determined by digestion with the enzymes HindIII for P-FMV, HindIII plus BamHI for ctp2-CP4-EPSPS, and EcoRI plus PstI for the E9 3' non-translated region. Additional experiments were performed with SacI plus XhoI for the P-FMV-ctp2-CP4 EPSPS region and for the E9 3' region. Plasmid DNA mixed with non-transgenic sugar beet DNA and non-transgenic sugar beet DNA alone were digested with the same enzymes, as positive and negative controls, respectively.

These enzymes cleave within the intended DNA insert, between the left and right T-DNA Borders (see the plasmid map in FIG. 1), so, if the respective elements are intact, the size of the hybridized fragments should be identical in H7-1 DNA and PV-BVGT08 DNA.

As an additional control the DNAs were digested with XbaI. XbaI cleaves once between the promoter and ctp2-CP4-EPSPS coding region. Therefore, one would expect a 8.6 kb fragment with the PV-BVGT08 DNA and in case of the H7-1 a border fragment which differs in size compared with the PV-BVGT08 fragment. The results are shown in FIGS. 6, 7, and 8.

Figure 6:
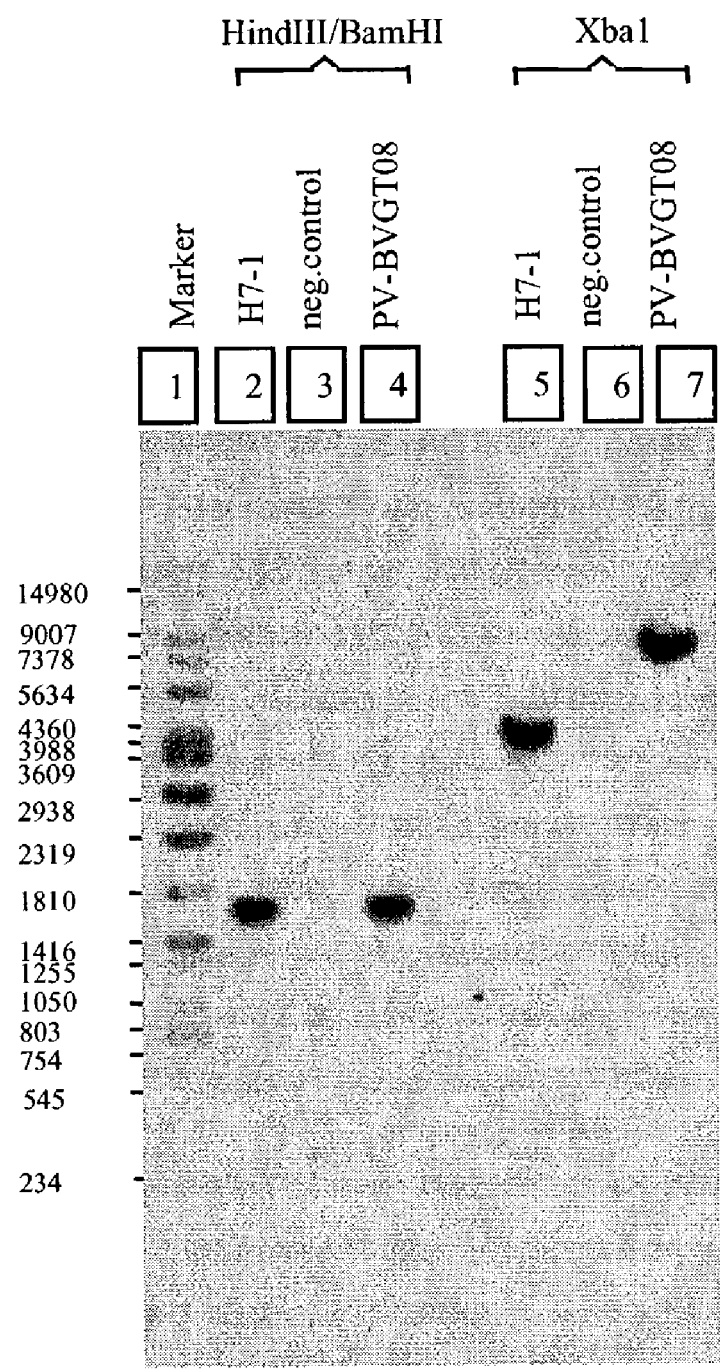
FIG. 6 Southern blot analysis of event H7-1 to evaluate ctp2-CP4-EPSPS coding region intactness. 10 µg of H7-1 genomic DNA, non-transgenic control DNA and non-transgenic control DNA mixed with PV-BVGT08 were digested with XbaI and HindIII/BamHI. The blot was probed with a $^{32}$P-labelled CP4-EPSPS-PCR fragment. The probe represents the sequence of PV-BVGT08, bp 447-1555.

FIG. 6: The digest with HindIII and BamHI released the CP4-EPSPS gene and the blot was probed with a CP4-EPSPS fragment generated by PCR. The negative control (lane 6) did not show any hybridisation bands. Genomic DNA from the event H7-1 and plasmid PV-BVGT08 mixed with non-transgenic DNA both produced an approximately 1.7 kb fragment which corresponds to the expected size. The digest with XbaI resulted in the expected 8.6 kb fragment of the linearized PV-BVGT08. For event H7-1 the digest resulted in the approximately 4.0 kb border fragment (see also FIGS. 4 and 5). Again, the negative control did not show any signal.

Figure 7:
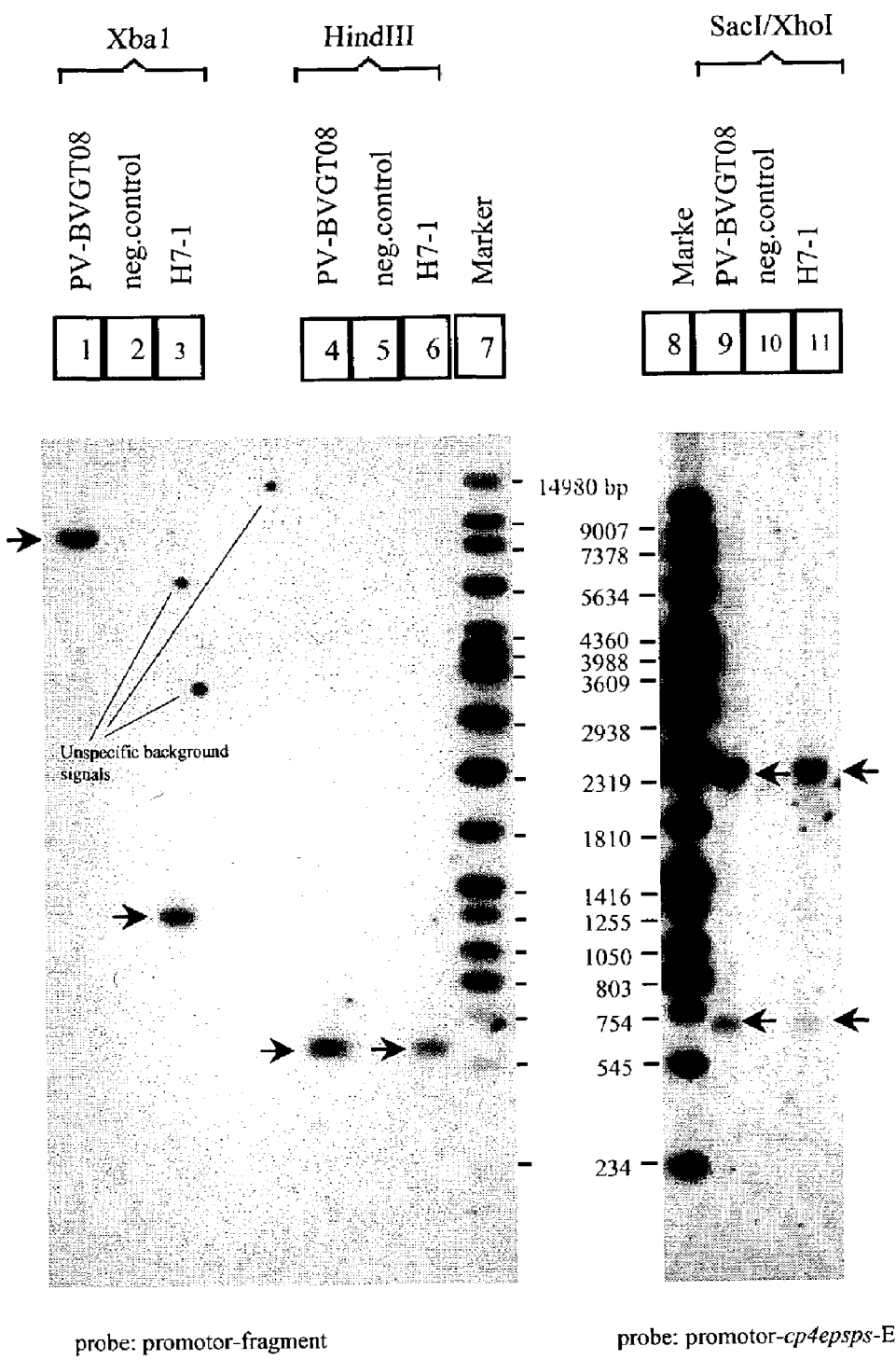
FIG. 7 Southern blot analysis of event H7-1 to evaluate promoter region intactness. 10 µg of H7-1 genomic DNA, non-transgenic control DNA and non-transgenic control DNA mixed with PV-BVGT08 were digested with HindIII, XbaI and SacI/XhoI. The blot was probed with a $^{32}$P-labelled promoter fragment (HindIII)(=PV-BVGT08 sequence, bp 7972-8583) or with the complete promotor-ctp2-CP4-EPSPS-E9-3'-cassette (PmeI/XhoI)(=PV-BVGT08 sequence, bp 7935-2389).
Figure 8:
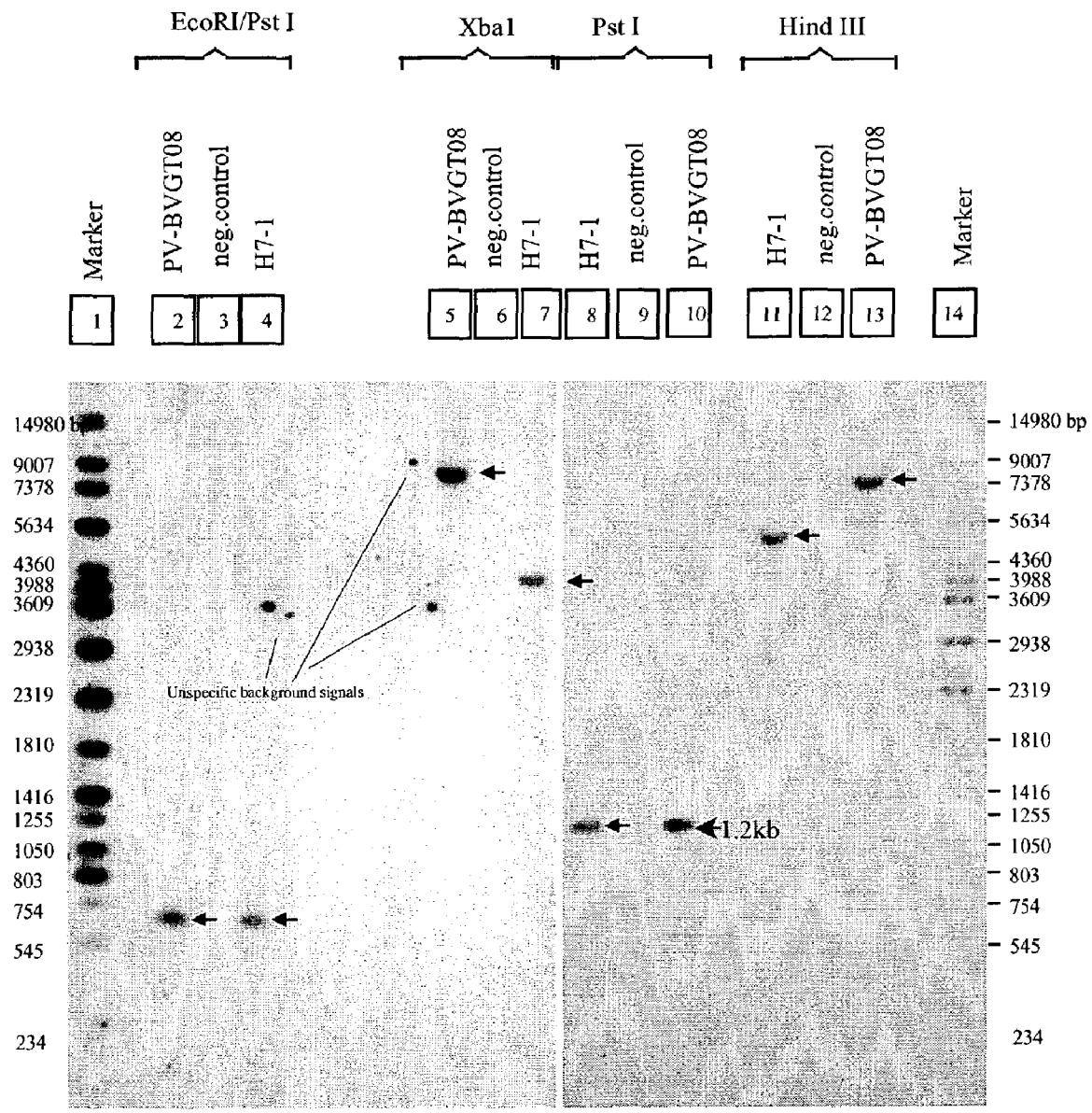
FIG. 8 Southern blot analysis of event H7-1 to evaluate polyadenylation region intactness. 10 µg of H7-1 genomic DNA, non-transgenic control DNA and non-transgenic control DNA mixed with PV-BVGT08 were digested with EcoRI/PstI, XbaI, HindIII, and PstI. The blot was probed with a $^{32}$P-labelled E9-3' polyadenylation fragment (BamHI/XhoI)(=PV-BVGT08 sequence, bp 1702-2389).

FIG. 7: The digest with HindIII released the Figwort mosaic virus promoter and the blot was probed with a promoter fragment generated by PCR. The negative control (lane 5) did not show any hybridization signals. Genomic DNA from event H7-1 and plasmid PV-BVGT08 mixed with non-transgenic DNA both produced a hybridizing fragment of 0.6 kb approximate size. This fragment corresponds to the expected size (lane 4 and 6) of the promoter.

The digest with XbaI resulted in the expected 8.6 kb fragment of the linearized PV-BVGT08 and in the approximately 1.3 kb left border fragment (lane 1 and 3) from event H7-1. This 1.3 kb fragment is also an additional proof that the event H7-1 contains only a single copy of the transgene. Again the negative control (lane 2) did not show any signal.

The digest with SacI/XhoI released the promotor together with the CP4-EPSPS coding region and the polyadenylation region. Hybridization with the complete promotor-ctp2-CP4-EPSPS-polyadenylation signal cassette (PmeI/XhoI fragment) produced the expected 2.3 kb promotor-ctp2-CP4-EPSPS and the 0.7 kb polyadenylation signal fragments both with the PV-BVGT08 DNA mixed with non-transgenic DNA and with H7-1 genomic DNA (lane 9 and 11).

FIG. 8: The digest with PstI and EcoRI released the E9-3' polyadenylation signal and the blot was probed with a polyadenylation signal fragment. The negative control (lane 3) did not show any hybridization bands. Plasmid PV-BVGT08 mixed with non-transgenic DNA and genomic DNA from the event H7-1 both produced an approximately 0.6 kb fragment which corresponds to the expected size. The digest with XbaI resulted in the expected 8.6 kb fragment of the linearized PV-BVGT08 and in an approximately 4.0 kb border fragment with event H7-1.

The digest with PstI released the E9-3'polyadenylation signal combined with a 0.5 kb 3'portion of the CP4-EPSPS coding region. The resulting 1.2 kb fragment was detectable as expected either with the H7-1 genomic DNA and also with the PV-BVGT08 DNA.

The digest with HindIII resulted in the 8.0 kb fragment of the linearized PV-BVGT08 minus the promoter fragment (lane 13) and in a 5.2 kb border fragment (lane 11) with H7-1. The single 5.2 kb fragment from the HindIII digest and the single 4.0 kb fragment from the XbaI digest are also an additional proof that the event H7-1 contains only one copy of inserted DNA. Again the negative controls did not show any signal.

In summary the results of the blots prove, that all elements of the transferred DNA are intact and that the event H7-1 contains a single intact CTP2-CP4-EPSPS coding region with its regulatory elements, the pFMV promoter and E9-3' transcriptional termination sequence.

4. Analysis for the Detection of Backbone Fragments

The backbone region of a Ti-plasmid is defined as the region outside of the T-DNA bounded with left and right border sequences, which consists of the ori genes and selection genes for bacterial replication and bacterial selection and which is normally not transferred to the plant genome by Agrobacterium mediated transformation. To confirm the absence of the backbone vector DNA in the event H7-1, genomic DNA from H7-1, from a non transformed control and genomic DNA from H7-1 mixed with PV-BVGT08 DNA was digested with the restriction enzyme XbaI and probed with three overlapping PCR generated probes, that encompassed the entire backbone sequence. A fourth probe consists of the whole backbone in one fragment.

Figure 9:
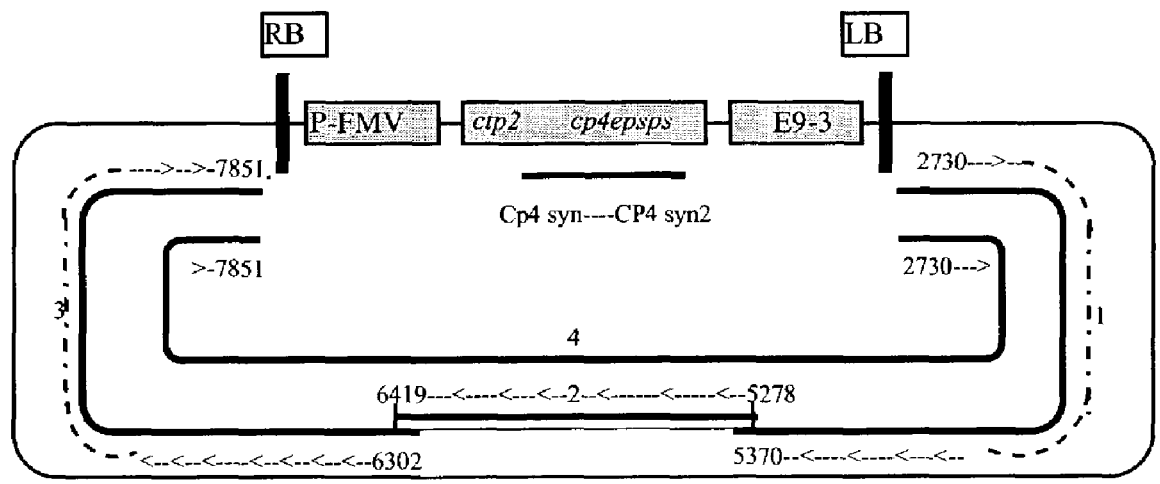
FIG. 9 Fragments used as probes to evaluate absence of backbone vector DNA in event H7-1.

The probes used represent the backbone sequence (see FIG. 9):
1: bp 2730-5370
2: bp 5278-6419
3: bp 6302-7851
4: bp 2730-7851

Figure 10:
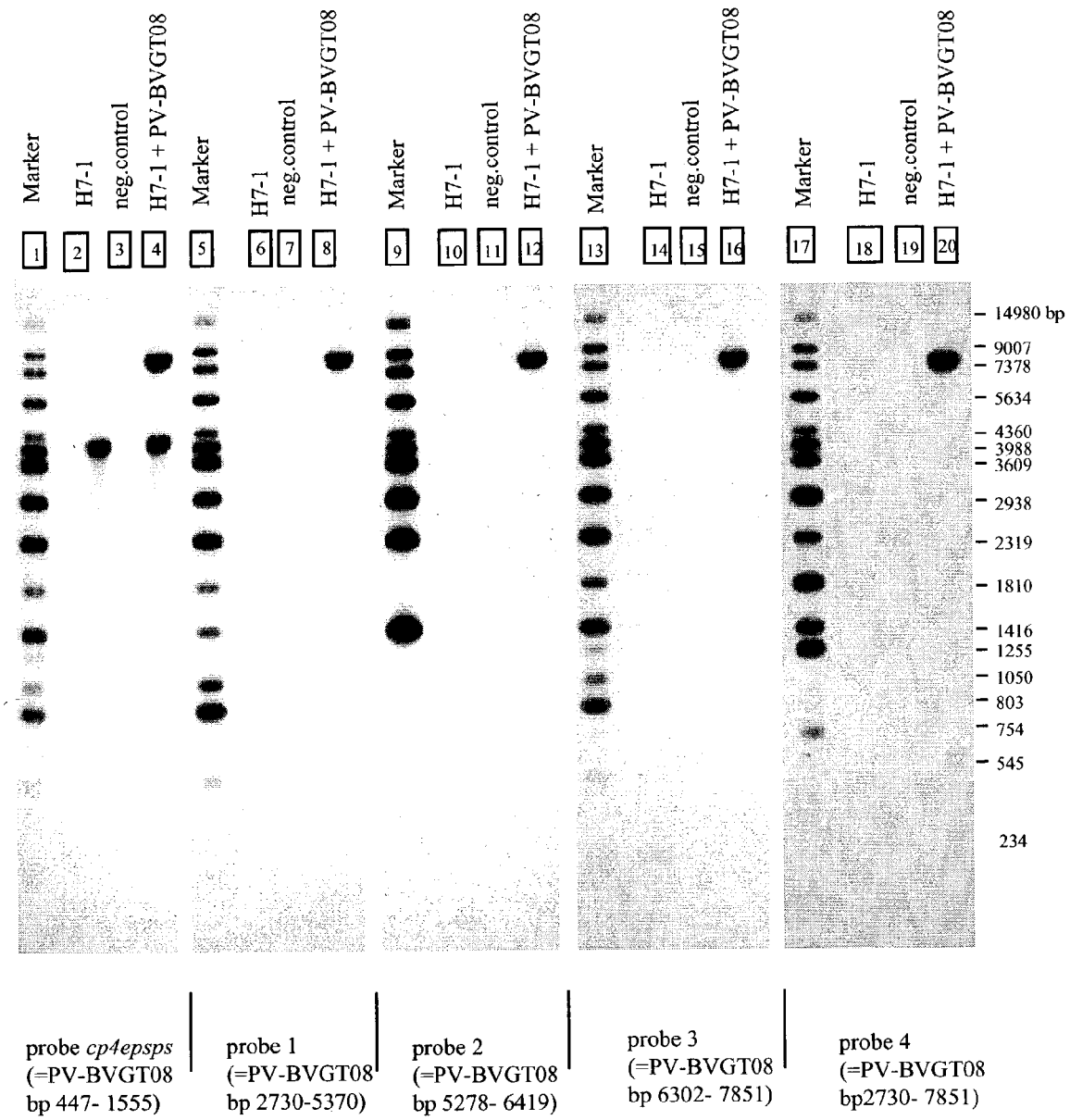
FIG. 10 Southern blot analysis of event H7-1 to evaluate absence of backbone vector DNA in event H7-1. 10 µg of H7-1 genomic DNA, non-transgenic control DNA and non-transgenic control DNA mixed with PV-BVGT08 were digested with XbaI. The blots were probed with $^{32}$P-labelled probes encompassing the entire backbone of PV-BVGT08 (probe 1-4). One blot was probed with a labelled CP4-EPSPS fragment.

FIG. 10 shows the result of the Southern blot analysis. Lanes 6, 10, 14, and 18: digest of H7-1 genomic DNA probed with the backbone fragments of the whole backbone did not show any hybridization bands. Only lanes 4, 8, 12, 16, and 20: H7-1 genomic DNA mixed with PV-BVGT08 DNA showed bands of 8.6 kb, as expected. The bands represent the linearized PV-BVGT08 DNA.

Lanes 2 and 4: H7-1 genomic DNA, and H7-1 genomic DNA mixed with PV-BVGT08, and hybridized with the CP4-EPSPS fragment, showed hybridizing signals. The 4 kb band in lane 2 represents the right border fragment, the two bands of lane 4 represent again the 4.0 kb right border fragment and the 8.6 kb linearized PV-BVGT08 plasmid. Both bands have the same intensity. This is a clear indication that the concentration of the added PV-BVGT08 DNA is comparable with the concentration of the CP4-EPSPS element in the H7-1 DNA. The concentration of the used plasmid DNA is equivalent to 0.5 copies. If there were backbone sequences integrated in the H7-1 genome, clear signals should be detectable.

These results prove that H7-1 does not contain any detectable backbone sequence of the plasmid used for the transformation. This result was also supported by the data of the analysis of the 5' and 3' genomic flanking regions (see below).

5. Identification of 5' and 3' Genomic Flanking Sequences

Agrobacterium mediated transformation normally leads to the integration of all sequences between the left and right border into the plant genome. The 5' and 3' ends of the integrated plasmid DNA should be within or near the left or the right border sequences, respectively. Therefore an Inverse-PCR technique was used to identify those regions. The cloned PCR products were sequenced and the sequence data were compared to PV-BVGT08 sequence.

FIG. 11 shows the alignment for the sequence from the cloned Inverse PCR fragment (D1U.RPT) (=genome H7-1, upper sequence), obtained with primers for analysis of the left border region, versus the PV-BVGT08 sequence (lower sequence). The comparison of both sequences showed that the homology stopped exactly within the border sequence.

Figure 12:
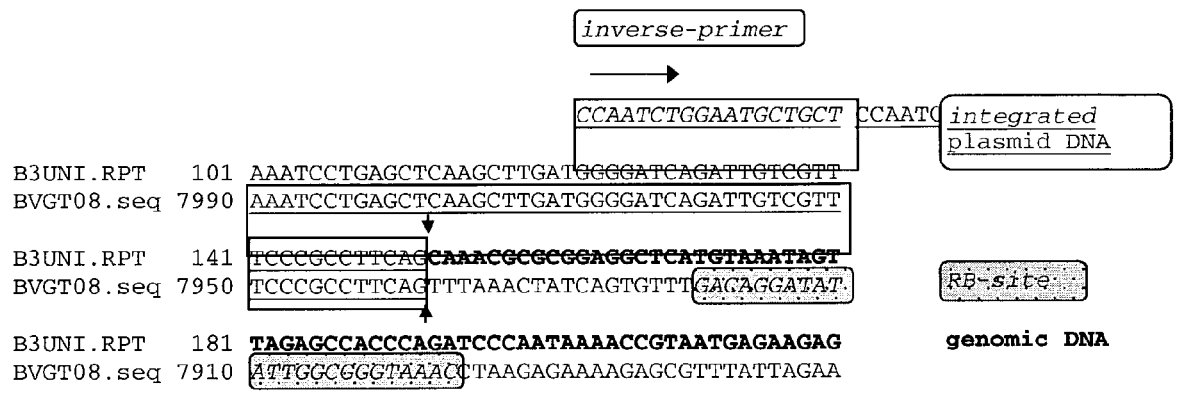
FIG. 12 Comparison between the PCR fragments and the PV-BVGT08 sequences on the right border region.

FIG. 12 shows the alignment for the sequence from the cloned Inverse-PCR fragment (B3UNI.RPT) (=genome H7-1, upper sequence), obtained with primers for analysis of the right border region, versus the PV-BVGT08 sequence (lower sequence). The comparison of both sequences showed that the homology stopped already 18 nucleotides in front of border sequence.

In total, this is a clear indication, that the sequence between the left and right borders of the Ti-plasmid PV-BVGT08 is integrated correctly. The sequence stopped within or immediately in front of the borders. These data support the results of the backbone analysis, that no sequences of the backbone outside the border regions were integrated into the H7-1 genome.

To determine whether the flanking sequences on the right or left side of the insert in sugar beet event H7-1 are intact plant genomic sequences, inverse PCR analysis with primer combinations P1, P2, P3 and P4 were performed.

The primers of primer combinations P1 and P2 are located outside of the insert. If the DNA of the insertion locus within event H7-1 is identical with DNA of a non-transformed control, the PCR should result in two PCR fragments representing synthesis from the two primer combinations. The primers of primer combinations P3 and P4 are designed in a way such that one of the respective primers is located inside the CP4-EPSPS insert and the other primer is located outside the insert, within the plant genomic DNA. So the PCR should produce fragments from the H7-1 event DNA only.

Sequence data from Inverse-PCR-technique combined with data from the PV-BVGT08 vector results in a sequence which includes the H7-1 insert (PV-BVGT08 sequence), the right and left junction regions and additional sugar beet genomic DNA (SEQ ID NO: 5).

For the identification of the transgene-to-plant genomic DNA junctions (identification of event specificity) and for the genomic DNA regions to the left and right sides of the insert following primer combinations were used:

P1 combination (primer for analyzing genomic DNA outside the right border region, SEQ ID NO: 18, SEQ ID NO: 19):

```
Upper primer: 5' CGG TAA ATG CAT TGG CCT TTG TT

Lower primer: 5' CAC CCA GAT CCC AAT AAA ACC GTA AT

Expected PCR-product 241 bp (SEQ ID NO: 20)
```

P2 combination (primer for analyzing genomic DNA outside the left border region, SEQ ID NO: 21, SEQ ID NO: 22):

```
Upper Primer:  5' AAA TGG TTG TAG ATA AAT AAG GAA
                  ATC A

Lower primer:  5' ACA TGT TTG AGC ACT CTT CTT GT

Expected PCR-product 377 bp (SEQ ID NO: 23)
```

P3 combination (primer for analyzing the transgene-to-plant genomic DNA junction, SEQ ID NO: 7, SEQ ID NO: 8):

```
Upper Primer:  5' ATG CAT TGG CCT TTG TTT TTG AT

Lower Primer:  5' TGT CGT TTC CCG CCT TCA G

Expected PCR-product 288 bp (SEQ ID NO: 11)
```

P4 combination (primer for analyzing the transgene-to-plant genomic DNA junction, SEQ ID NO: 9, SEQ ID NO: 10):

```
Upper Primer:  5' CGC TGC GGA CAT CTA CAT TTT TGA
                  AT

Lower primer:  5' AGT TAA CTT TCC ACT TAT CGG GGC
                  ACT G

Expected PCR-product 751 bp (SEQ ID NO: 12)
```

Figure 13:
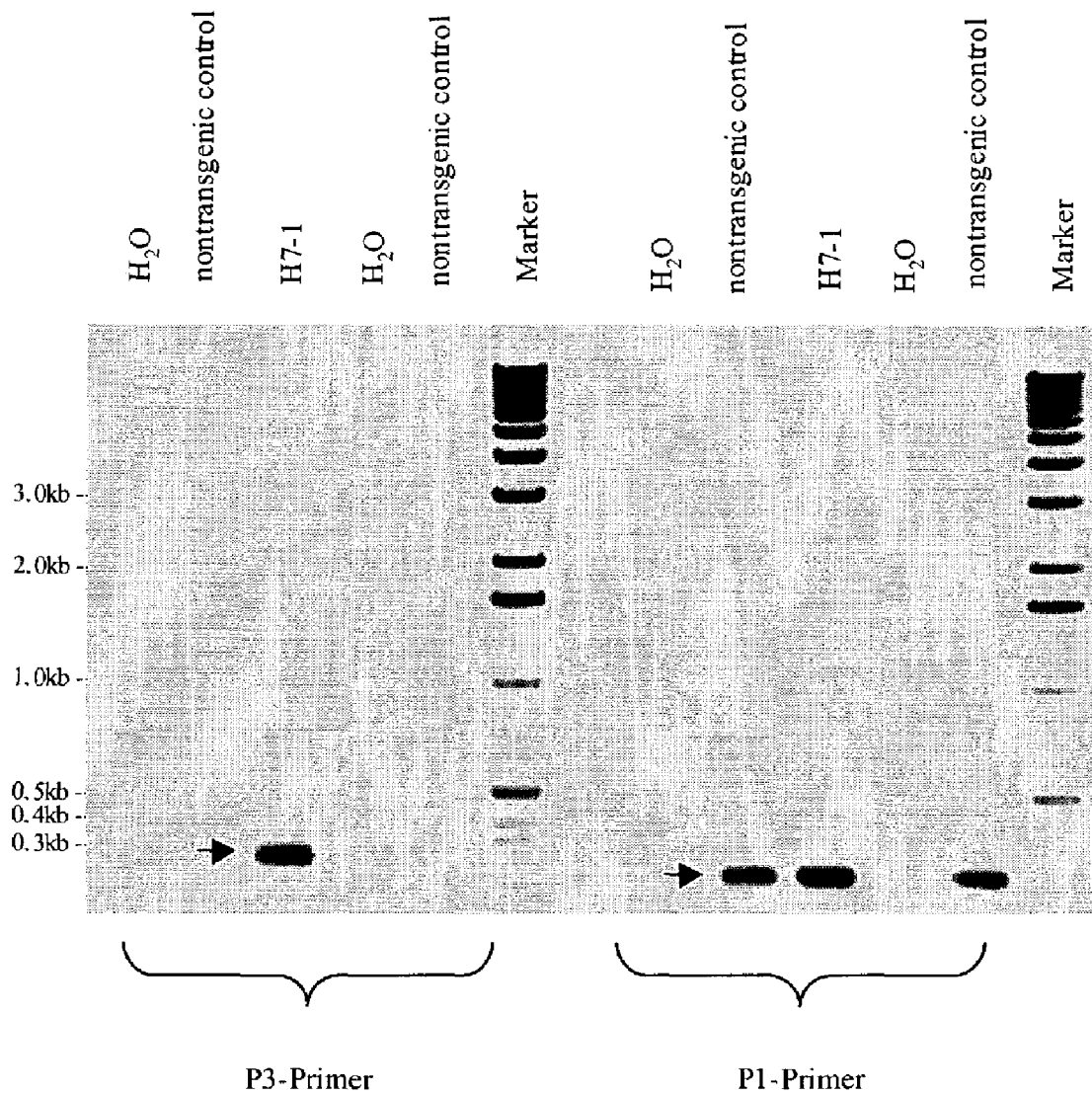
FIG. 13 Analysis of the genomic DNA outside the right junction of the insert. Approximately 50 ng of either event H7-1 genomic DNA, non-transgenic control DNA or water were used for PCR reactions with the primer combinations P1, where both primers are located outside of the insert, and P3, where one primer is located within the insert and the other primer lies outside the insert.

PCR Experiments with Event H7-1 DNA and with DNA from a non-transgenic control plant, using the primer combination P3, which has one primer being located within the H7-1 insert, yields a fragment with the event H7-1 DNA only. In contrast, PCR experiments using the primer combination P1, homologous to sequences outside the insert, yield fragments with both event H7-1 and non-transgenic control DNA. See FIG. 13 for these results.

The results indicate that the sequence next to the right junction of the insert is present in the transgenic event H7-1 DNA and in the DNA from non-transgenic plants. It can be concluded that this DNA outside the event H7-1 insert is non-transgenic genomic DNA.

Figure 14:
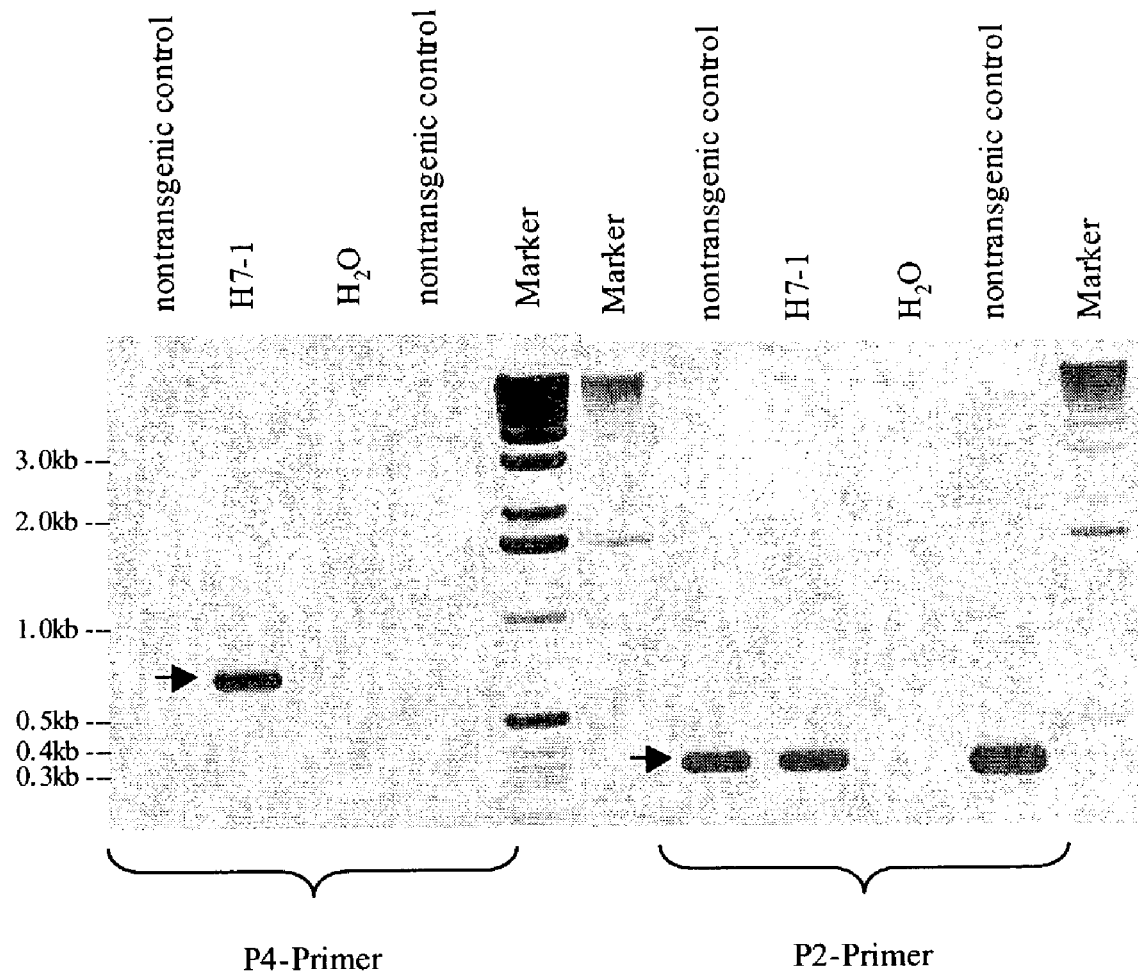
FIG. 14 Analysis of the genomic DNA outside the left junction of the insert. Approximately 50 ng of H7-1 genomic DNA, non-transgenic control DNA and water were used for PCR-reactions with the primer combinations P2, where both primers are located outside of the insert, and P4, where one primer is located within the insert and the other primer lies outside the insert.

PCR experiments conducted with event H7-1 DNA and DNA from a non-transgenic control plant using primer combination P4, which has one of the primers located inside the CP4-EPSPS insert, yields a fragment with the event H7-1 DNA only. In contrast, PCR experiments using the primer combination P2, homologous to sequences outside the insert, yield fragments with both event H7-1 and non-transgenic control DNA. See FIG. 14 for these results.

The results indicate that the sequence next to the left junction of the insert is present both in the transgenic event H7-1 DNA and in the DNA from non-transgenic plants. It can be concluded that the DNA outside the left junction is non-transgenic genomic DNA.

In summary, it can be stated that the sequences outside of the sugar beet event H7-1 insert are identical with sequences present in non-transgenic plants. It can be concluded that these sequences are plant genomic sequences present in the parental line used for transformation and in other conventional sugar beet lines.

6. Stability Over Generations

Figure 15:
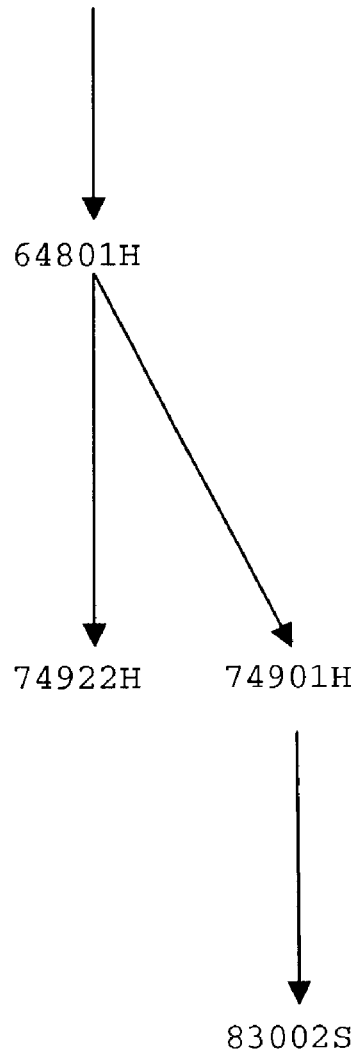
FIG. 15 Progeny map of H71-1 seed lots.

To demonstrate the stability of the integrated DNA the original transformation event H7-1 was compared with three progenies (64801H, 74922H, and 83002S; see FIG. 15) of this line resulting from self pollination with non-transgenic sugar beet lines. The original transformed line and the progenies were produced in 1995, 1996, 1997, and 1998.

AS controls four different non-transgenic sugar beet lines were analysed (3S0057, 5R7150, 8K1180, 6S0085). All DNAS were digested with XbaI, HindIII, and BamHI, respectively, and hybridized with a labelled CP4-EPSPS fragment. To demonstrate that the T-DNA is stably integrated in the plant genome, all lanes of the H7-1 progenies digested with the same restriction enzyme should show a band of exact the same size.

Figure 16:
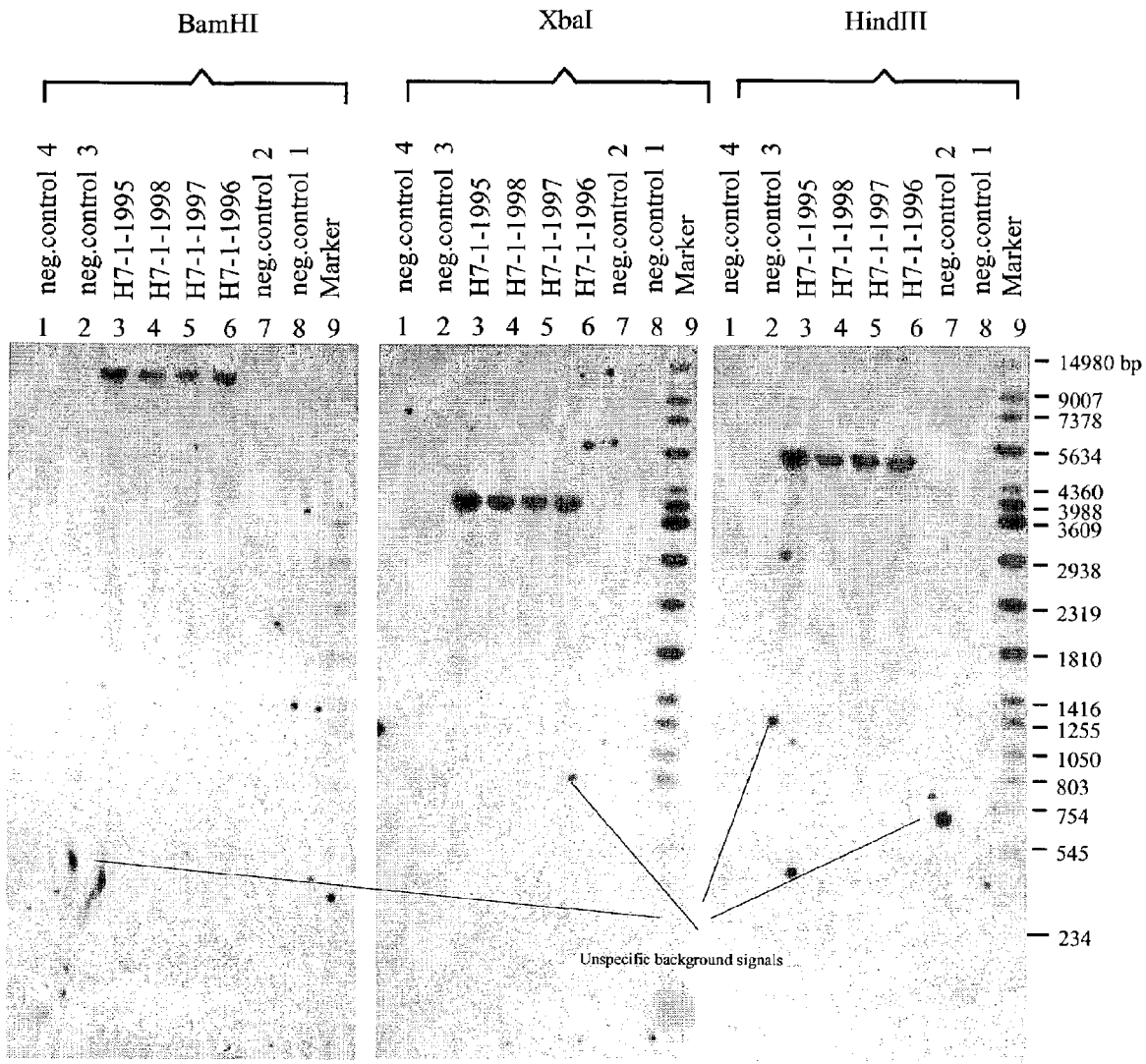
FIG. 16 Southern blot analysis of event H7-1 to evaluate whether the inserted DNA is stably integrated into the genome. 10 μg of H7-1 genomic DNAs (the original transformant H7-1-1995 and three progenies, H7-1-1996 to 1998) and non-transgenic control DNAs from different origins were digested with BamHI, XbaI, and HindIII. The blot was probed with a $^{32}$P-labelled CP4-EPSPS probe of PV-BVGT08 (=bp 447-1555).

The DNAs from the progenies of H7-1 lanes 3 to 6 show the expected fragments: DNA digested with BamHI resulted in bands of approximately 11 kb, digests with XbaI produced fragments of 4.0 kb and HindIII restriction produced bands of 5.2 kb. All bands from the same restriction but from different years were identical in their size. All non-transgenic lines did not show any signal (FIG. 16).

These results demonstrate that the introduced sequence is stably integrated into the genomic DNA and stably inherited.

The invention claimed is:

1. An event H7-1 sugar beet plant comprising a transgenic insert that comprises a transgene which confers glyphosate tolerance, wherein the event H7-1 plant can be identified by using a pair of primers, at least one of which hybridizes to genomic DNA outside of the insert, and wherein the pair of primers can be used in polymerase chain reaction to amplify from the DNA of said sugar beet plant, cells, tissues or seeds thereof, a DNA fragment comprising genomic DNA and DNA of at least part of the insert, wherein the amplified fragment and pair of primers are selected from the group consisting of:
   (a) a DNA fragment of 630-700 bp that can be amplified using a first primer having the nucleotide sequence of SEQ ID NO: 1 and a second primer having the nucleotide sequence of SEQ ID NO: 2;
   (b) a DNA fragment of 3500-3900 bp that can be amplified using a first primer having the nucleotide sequence of SEQ ID NO: 3 and a second primer having the nucleotide sequence of SEQ ID NO: 4;
   (c) a DNA fragment of 270-300 bp that can be amplified using a first primer having the nucleotide sequence of SEQ ID NO: 7 and a second primer having the nucleotide sequence of SEQ ID NO: 8;
   (d) a DNA fragment of 710-790 bp that can be amplified a first primer having the nucleotide sequence of SEQ ID NO: 9 and a second primer having the nucleotide sequence of SEQ ID NO: 10;
   (e) a DNA fragment of 990-1100 bp that can be amplified a first primer having the nucleotide sequence of SEQ ID NO: 14 and a second primer having the nucleotide sequence of SEQ ID NO: 16; and
   (f) any combination of elements (a) through (e).

2. The event H7-1 sugar beet plant according to claim 1, wherein the DNA fragment of (a) is a 664 bp DNA fragment having the nucleotide sequence of SEQ ID NO: 13.

3. The event H7-1 sugar beet plant according to claim 1, wherein the DNA fragment of (b) is a 3706 bp DNA fragment having the nucleotide sequence of SEQ ID NO: 6.

4. The event H7-1 sugar beet plant according to claim 1, wherein the DNA fragment of (c) is a 288 bp DNA fragment having the nucleotide sequence of SEQ ID NO: 11.

5. The event H7-1 sugar beet plant according to claim 1, wherein the DNA fragment of (d) is a 751 bp DNA fragment having the nucleotide sequence of SEQ ID NO: 12.

6. The event H7-1 sugar beet plant according to claim 1, wherein the DNA fragment of (e) is a 1042 bp DNA fragment having the nucleotide sequence of SEQ ID NO: 17.

7. A seed representative of seed deposited with the NCIMB and having the accession number NCIMB 41158 or NCIMB 41159.

8. A transgenic sugar beet plant obtained from seed of claim 7.

9. The event H7-1 sugar beet plant according to claim 1, wherein the DNA fragment is selected from the group consisting of:
   (i) a 664 bp DNA fragment according to (a) having the nucleotide sequence of SEQ ID NO: 13;
   (ii) a 3706 bp DNA fragment according to (b) having the nucleotide sequence of SEQ ID NO: 6;
   (iii) a 288 bp DNA fragment according to (c) having the nucleotide sequence of SEQ ID NO: 11;
   (iv) a 751 bp DNA fragment according to (d) having the nucleotide sequence of SEQ ID NO: 12;
   (v) a 1042 bp DNA fragment according to (e) having the nucleotide sequence of SEQ ID NO: 17; and
   (vi) any combination thereof.

10. An event H7-1 sugar beet seed comprising a transgenic insert that comprises a transgene which confers glyphosate tolerance, wherein the event H7-1 seed can be identified by using a pair of primers, at least one of which hybridizes to genomic DNA outside of the insert, and wherein the pair of primers can be used in polymerase chain reaction to amplify from the DNA of said seed a DNA fragment comprising genomic DNA and DNA of at least part of the insert, wherein the amplified fragment and pair of primers are selected from the group consisting of:
   (a) a DNA fragment of 630-700 bp that can be amplified using a first primer having the nucleotide sequence of SEQ ID NO: 1 and a second primer having the nucleotide sequence of SEQ ID NO: 2;
   (b) a DNA fragment of 3500-3900 bp that can be amplified using a first primer having the nucleotide sequence of SEQ ID NO: 3 and a second primer having the nucleotide sequence of SEQ ID NO: 4;
   (c) a DNA fragment of 270-300 bp that can be amplified using a first primer having the nucleotide sequence of SEQ ID NO: 7 and a second primer having the nucleotide sequence of SEQ ID NO: 8;
   (d) a DNA fragment of 710-790 bp that can be amplified a first primer having the nucleotide sequence of SEQ ID NO: 9 and a second primer having the nucleotide sequence of SEQ ID NO: 10;
   (e) a DNA fragment of 990-1100 bp that can be amplified a first primer having the nucleotide sequence of SEQ ID NO: 14 and a second primer having the nucleotide sequence of SEQ ID NO: 16; and
   (f) any combination of elements (a) through (e).

11. The event H7-1 sugar beet seed according to claim 10, wherein the DNA fragment is selected from the group consisting of:
   (i) a 664 bp DNA fragment according to (a) having the nucleotide sequence of SEQ ID NO: 13;
   (ii) a 3706 bp DNA fragment according to (b) having the nucleotide sequence of SEQ ID NO: 6;
   (iii) a 288 bp DNA fragment according to (c) having the nucleotide sequence of SEQ ID NO: 11;
   (iv) a 751 bp DNA fragment according to (d) having the nucleotide sequence of SEQ ID NO: 12;
   (v) a 1042 bp DNA fragment according to (e) having the nucleotide sequence of SEQ ID NO: 17; and
   (vi) any combination thereof.

12. The event H7-1 sugar beet seed according to claim 10, wherein the DNA fragment of (a) is a 664 bp DNA fragment having the nucleotide sequence of SEQ ID NO: 13.

13. The event H7-1 sugar beet seed according to claim 10, wherein the DNA fragment of (b) is a 3706 bp DNA fragment having the nucleotide sequence of SEQ ID NO: 6.

14. The event H7-1 sugar beet seed according to claim 10, wherein the DNA fragment of (c) is a 288 bp DNA fragment having the nucleotide sequence of SEQ ID NO: 11.

15. The event H7-1 sugar beet seed according to claim 10, wherein the DNA fragment of (d) is a 751 bp DNA fragment having the nucleotide sequence of SEQ ID NO: 12.

16. The event H7-1 sugar beet seed according to claim 10, wherein the DNA fragment of (e) is a 1042 bp DNA fragment having the nucleotide sequence of SEQ ID NO: 17.

17. An event H7-1 sugar beet cell, tissue or part, comprising a transgenic insert that comprises a transgene which confers glyphosate tolerance, wherein the event H7-1 cell, tissue or part, can be identified by using a pair of primers, at least one of which hybridizes to genomic DNA outside of the insert, and wherein the pair of primers can be used in polymerase chain reaction to amplify from the DNA of said cell, tissue or part, a DNA fragment comprising genomic DNA and DNA of at least part of the insert, wherein the amplified fragment and pair of primers are selected from the group consisting of:

(a) a DNA fragment of 630-700 bp that can be amplified using a first primer having the nucleotide sequence of SEQ ID NO: 1 and a second primer having the nucleotide sequence of SEQ ID NO: 2;

(b) a DNA fragment of 3500-3900 bp that can be amplified using a first primer having the nucleotide sequence of SEQ ID NO: 3 and a second primer having the nucleotide sequence of SEQ ID NO: 4;

(c) a DNA fragment of 270-300 bp that can be amplified using a first primer having the nucleotide sequence of SEQ ID NO: 7 and a second primer having the nucleotide sequence of SEQ ID NO: 8;

(d) a DNA fragment of 710-790 bp that can be amplified a first primer having the nucleotide sequence of SEQ ID NO: 9 and a second primer having the nucleotide sequence of SEQ ID NO: 10;

(e) a DNA fragment of 990-1100 bp that can be amplified a first primer having the nucleotide sequence of SEQ ID NO: 14 and a second primer having the nucleotide sequence of SEQ ID NO: 16; and (f) any combination of elements (a) through (e).

18. The event H7-1 sugar beet cell, tissue or part according to claim 17, wherein the DNA fragment is selected from the group consisting of:

(i) a 664 bp DNA fragment according to (a) having the nucleotide sequence of SEQ ID NO: 13;

(ii) a 3706 bp DNA fragment according to (b) having the nucleotide sequence of SEQ ID NO: 6;

(iii) a 288 bp DNA fragment according to (c) having the nucleotide sequence of SEQ ID NO: 11;

(iv) a 751 bp DNA fragment according to (d) having the nucleotide sequence of SEQ ID NO: 12;

(v) a 1042 bp DNA fragment according to (e) having the nucleotide sequence of SEQ ID NO: 17; and (vi) any combination thereof.

19. The event H7-1 sugar beet cell, tissue or part according to claim 17, wherein the DNA fragment of (a) is a 664 bp DNA fragment having the nucleotide sequence of SEQ ID NO: 13.

20. The event H7-1 sugar beet cell, tissue or part according to claim 17, wherein the DNA fragment of (b) is a 3706 bp DNA fragment having the nucleotide sequence of SEQ ID NO: 6.

21. The event H7-1 sugar beet cell, tissue or part according to claim 17, wherein the DNA fragment of (c) is a 288 bp DNA fragment having the nucleotide sequence of SEQ ID NO: 11.

22. The event H7-1 sugar beet cell, tissue or part according to claim 17, wherein the DNA fragment of (d) is a 751 bp DNA fragment having the nucleotide sequence of SEQ ID NO: 12.

23. The event H7-1 sugar beet cell, tissue or part according to claim 17, wherein the DNA fragment of (e) is a 1042 bp DNA fragment having the nucleotide sequence of SEQ ID NO: 17.

24. An event H7-1 sugar beet plant comprising a transgene that confers glyphosate tolerance, wherein the event H7-1 plant can be identified by using a pair of primers, at least one of which hybridizes to genomic DNA outside of the transgene, and wherein the two primers can be used in polymerase chain reaction to amplify from the DNA of said sugar beet plant, cells, tissues or seeds thereof, a DNA fragment comprising genomic DNA and DNA of at least part of the transgene, wherein the amplified fragment and pair of primers are a DNA fragment of 630-700 bp that can be amplified using a first primer having the nucleotide sequence of SEQ ID NO: 1 and a second primer having the nucleotide sequence of SEQ ID NO: 2.

25. The event H7-1 sugar beet plant according to claim 24, wherein the DNA fragment is a 664 bp DNA fragment having the nucleotide sequence of SEQ ID NO: 13.

26. An event H7-1 sugar beet plant comprising a transgene that confers glyphosate tolerance, wherein the event H7-1 plant can be identified by using a pair of primers, at least one of which hybridizes to genomic DNA outside of the transgene, and wherein the two primers can be used in polymerase chain reaction to amplify from the DNA of said sugar beet plant, cells, tissues or seeds thereof, a DNA fragment comprising genomic DNA and DNA of at least part of the transgene, wherein the amplified fragment and pair of primers are a DNA fragment of 3500-3900 bp that can be amplified using a first primer having the nucleotide sequence of SEQ ID NO: 3 and a second primer having the nucleotide sequence of SEQ ID NO: 4.

27. The event H7-1 sugar beet plant according to claim 26, wherein the DNA fragment is a 3706 bp DNA fragment having the nucleotide sequence of SEQ ID NO: 6.

28. An event H7-1 sugar beet plant comprising a transgene that confers glyphosate tolerance, wherein the event H7-1 plant can be identified by using a pair of primers, at least one of which hybridizes to genomic DNA outside of the transgene, and wherein the two primers can be used in polymerase chain reaction to amplify from the DNA of said sugar beet plant, cells, tissues or seeds thereof, a DNA fragment comprising genomic DNA and DNA of at least part of the transgene, wherein the amplified fragment and pair of primers are a DNA fragment of 990-1100 bp that can be amplified a first primer having the nucleotide sequence of SEQ ID NO: 14 and a second primer having the nucleotide sequence of SEQ ID NO: 16.

29. The event H7-1 sugar beet plant according to claim 28, wherein the DNA fragment is a 1042 bp DNA fragment having the nucleotide sequence of SEQ ID NO: 17.

30. An event H7-1 sugar beet seed comprising a transgene that confers glyphosate tolerance, wherein the event H7-1 seed can be identified by using a pair of primers, at least one of which hybridizes to genomic DNA outside of the transgene, and wherein the two primers can be used in polymerase chain reaction to amplify from the DNA of said sugar beet seed, a DNA fragment comprising genomic DNA and DNA of at least part of the transgene, wherein the amplified fragment and pair of primers are a DNA fragment of 630-700 bp that can be amplified using a first primer having the nucleotide sequence of SEQ ID NO: 1 and a second primer having the nucleotide sequence of SEQ ID NO: 2.

31. The event H7-1 sugar beet seed according to claim 30, wherein the DNA fragment is a 664 bp DNA fragment having the nucleotide sequence of SEQ ID NO: 13.

32. An event H7-1 sugar beet seed comprising a transgene that confers glyphosate tolerance, wherein the event H7-1 seed can be identified by using a pair of primers, at least one of which hybridizes to genomic DNA outside of the transgene, and wherein the two primers can be used in polymerase chain reaction to amplify from the DNA of said sugar beet seed, a DNA fragment comprising genomic DNA and DNA of at least part of the transgene, wherein the amplified fragment and pair of primers are a DNA fragment of 3500-3900 bp that can be amplified using a first primer having the nucleotide sequence of SEQ ID NO: 3 and a second primer having the nucleotide sequence of SEQ ID NO: 4.

33. The event H7-1 sugar beet seed according to claim 32, wherein the DNA fragment is a 3706 bp DNA fragment having the nucleotide sequence of SEQ ID NO: 6.

34. An event H7-1 sugar beet seed comprising a transgene that confers glyphosate tolerance, wherein the event H7-1 seed can be identified by using a pair of primers, at least one of which hybridizes to genomic DNA outside of the transgene, and wherein the two primers can be used in polymerase chain reaction to amplify from the DNA of said sugar beet seed, a DNA fragment comprising genomic DNA and DNA of at least part of the transgene, wherein the amplified fragment and pair of primers are a DNA fragment of 990-1100 bp that can be amplified a first primer having the nucleotide sequence of SEQ ID NO: 14 and a second primer having the nucleotide sequence of SEQ ID NO: 16.

35. The event H7-1 sugar beet seed according to claim 34, wherein the DNA fragment is a 1042 bp DNA fragment having the nucleotide sequence of SEQ ID NO: 17.

* * * * *